United States Patent [19]

Arai et al.

[11] 4,241,168
[45] * Dec. 23, 1980

[54] PHOTOGRAPHIC COUPLER

[75] Inventors: Atsuaki Arai; Keisuke Shiba; Minoru Yamada; Nobuo Furutachi, all of Minami-ashigara, Japan

[73] Assignee: Fuji Photo Film Co., Ltd., Minami-ashigara, Japan

[*] Notice: The portion of the term of this patent subsequent to Feb. 28, 1995, has been disclaimed.

[21] Appl. No.: 835,278

[22] Filed: Sep. 21, 1977

Related U.S. Application Data

[63] Continuation of Ser. No. 604,364, Aug. 13, 1975, abandoned.

[30] Foreign Application Priority Data

Aug. 13, 1974 [JP] Japan .................................. 49-92685

[51] Int. Cl.² .............................................. G03C 1/40
[52] U.S. Cl. .................................. 430/503; 430/555; 430/558
[58] Field of Search .................... 96/100, 100 N, 56.5, 96/74

[56] References Cited

U.S. PATENT DOCUMENTS

| | | | |
|---|---|---|---|
| 3,930,866 | 1/1976 | Oishi et al. ............................. | 96/100 |
| 3,933,500 | 1/1976 | Shiba et al. ........................ | 96/100 N |
| 3,935,015 | 1/1976 | Arai et al. ............................. | 96/100 |
| 4,046,575 | 9/1977 | Boie et al. ............................ | 96/100 N |
| 4,076,533 | 2/1978 | Ota et al. ............................ | 96/100 N |

*Primary Examiner*—J. Travis Brown
*Attorney, Agent, or Firm*—Sughrue, Rothwell, Mion, Zinn & Macpeak

[57] ABSTRACT

A photographic two-equivalent magenta coupler represented by the following general formula (I):

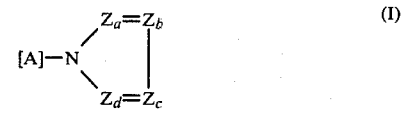

wherein [A] represents a magenta color image-forming coupler residue, and the

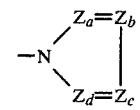

moiety represents a group replacing a hydrogen atom of an active methylene group in coupler [A] wherein $Z_a$, $Z_b$, $Z_c$ and $Z_d$, which can be the same or different, each represents a methine group or an —N= group, and the nitrogen-containing ring formed by $Z_a$ to $Z_d$ may further be substituted with a fused ring, with the proviso that the

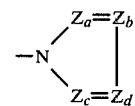

moiety does not represent a benzotriazolyl-1, benzotriazolyl-2, benzimidazolyl-1 or indazolyl-1 group; a photographic light sensitive material containing the photographic coupler; and a method of forming images using the photographic coupler.

12 Claims, No Drawings

PHOTOGRAPHIC COUPLER

This is a Continuation of application Ser. No. 604,364, filed Aug. 13, 1975, now abandoned.

BACKGROUND OF THE INVENTION

1. Field of the Invention

The present invention relates to a photographic coupler and, more particularly, to a novel 2-equivalent magenta coupler for use in a silver halide color photographic light-sensitive material.

2. Description of the Prior Art

It is known that, upon color development of a silver halide color photographic material, an oxidized aromatic primary amine color developing agent reacts with a coupler to form an indophenol, indoaniline, indamine, azomethine, phenoxazine, phenazine or like dye, with color images being formed. In this system, color reproduction is usually based on subtractive color photography, and silver halide emulsions selectively sensitive to blue, green and red light, respectively, and yellow, magenta and cyan color image-forming compounds which are in a complementary color relation to the sensitivity of the respective emulsions are employed. For example, acylacetanilide or dibenzoylmethane couplers are used for the formation of a yellow color image, pyrazolone, pyrazolobenzimidazole, cyanoacetophenone and indazolone couplers are mainly used for the formation of magenta color images, and phenolic couplers (e.g., phenols and naphthols) are mainly used for the formation of cyan color images.

In one of the most preferred embodiments of color photographic light-sensitive materials, dye image-forming couplers are added to silver halide emulsions. Couplers added to emulsions must be rendered non-diffusible (or diffusion-resistant.)

Almost all conventional color image-forming couplers are 4-equivalent couplers. That is, the development of 4 moles of silver halide as an oxidizing agent is theoretically necessary to form 1 mol of dye through the coupling reaction. On the other hand, 2-equivalent couplers having an active methylene group substituted with a group eliminatable upon the oxidative coupling with an oxidation product of an aromatic primary amine developing agent requires the development of only 2 moles of silver halide to form 1 mol of dye. Since 2-equivalent couplers require only one-half the silver halide as compared with ordinary 4-equivalent couplers to form a dye, their use enables the rapid processing of light-sensitive materials due to the thinness of the light-sensitive layers, the photographic properties to be improved due to a reduction in film thickness, and economic advantages to be achieved.

Several approaches have thus far been suggested to produce 2-equivalent 5-pyrazolone couplers mainly used as magenta-forming couplers. For example, the substitution of the 4-position of a pyrazolone with a thiocyano group is described in U.S. Pat. Nos. 3,214,437 and 3,253,924, with an acyloxy group is described in U.S. Pat. NO. 3,311,476, with an aryloxy group is described in U.S. Pat. No. 3,419,391, with a 2-triazolyl group is described in U.S. Pat. No. 3,617,291, and with a halogen atom is described in U.S. Pat. No. 3,522,052.

However, in using these 4-position substituted pyrazolone couplers, the disadvantages that serious color fog results, that the reactivity of the couplers is unsuitable, that the couplers are chemically so unstable that they are converted to materials incapable of color formation with the lapse of time, so that synthesis of the couplers often is difficult occur.

Also, it has hitherto been known to substitute the 4-position of a 5-pyrazolone with an alkylthio group, an arylthio group or a heterocyclic ring thio group as described in U.S. Pat. No. 3,227,554. However, with many of these known thio-substituted pyrazolone compounds, the reactivity with an oxidation product of an aromatic primary amino color developing agent is unsuitable and, further, they are difficult to employ in ordinary color light-sensitive materials due to the strong photographic action of the mercapto compound produced as a result of the coupling reaction. In addition, the chemical stability of these couplers is not satisfactory.

SUMMARY OF THE INVENTION

Therefore, an object of the present invention to provide a novel 2-equivalent magenta coupler in which the coupling position is substituted with a group eliminatable upon coupling with an oxidation product of an aromatic primary amine developing agent.

Another object of the present invention is to provide a novel 2-equivalent magenta coupler having suitable reactivity and capable of forming a dye in high yield without forming undesired fog or stain.

A further object of the present invention is to provide a color photographic light-sensitive material having a silver halide emulsion layer containing a novel magenta color image-forming coupler.

A still a further object of the present invention is to provide a process for reducing the amount of silver halide in a photographic emulsion layer by using a novel magenta color image-forming coupler therein, thus improving the sharpness of color images to be obtained.

A still further object of the present invention is to provide a color photographic having a fast color image by using a novel magenta color image-forming coupler.

An even further object of the present invention is to provide a novel 2-equivalent magenta coupler which can be synthesized with ease and in high yield.

Also an object of the present invention is to provide a 2-equivalent magenta coupler showing improved degree of conversion to the dye, having improved resistance against a reduction in coloration due to the attack of chemicals, and having excellent coloration reactivity.

These and other objects of the present invention will become apparent from the following detailed description and examples.

The objects of the present invention are attained in one embodiment with a photographic coupler represented by the following general formula (I),

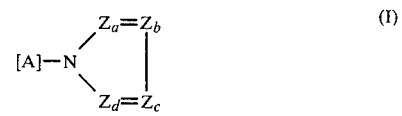

wherein [A] represents a magenta color image-forming coupler residue, and the

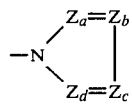

moiety represents a group replacing a hydrogen atom of the active methylene group in coupler [A], i.e., a group substituted in the coupling position, wherein $Z_a$, $Z_b$, $Z_c$ and $Z_d$ which may be the same or different, each represents an unsubstituted or substituted methine group, or an —N=group, in which the nitrogen-containing ring formed by $Z_a$ to $Z_d$ can further be combined with a fused ring, with the proviso that the

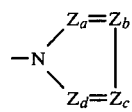

moiety does not represent a benzotriazolyl-1 group, a benzotriazolyl-2 group, an indazolyl-1 group or a benzimidazolyl group.

In another embodiment of the invention, the invention provides a color photographic light-sensitive material comprising a support having thereon at least one silver halide emulsion layer, with at least one of the silver halide emulsion layers containing a 2-equivalent magenta coupler represented by the general formula (I) above.

DETAILED DESCRIPTION OF THE INVENTION

In the coupler of the present invention represented by the general formula (I); the

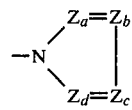

moiety does not represent a benzotriazolyl-1 group or a benzotriazolyl-2 group because these groups become development-inhibiting benzotriazoles upon elimination upon color development, with one of the objects of the present invention thus not being achieved.

In the above general formula, [A] can be any magenta color image-forming coupler residue and, preferably, [A] represents a 5-oxo-4-pyrazolonyl group or a 3-pyrazolo[1,5-a]-benzimidazolyl group.

Particularly useful couplers of the general formula (I) in accordance with the present invention are represented by the following general formulae (II) and (III);

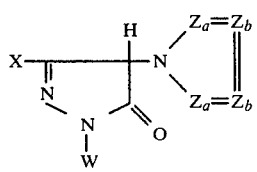

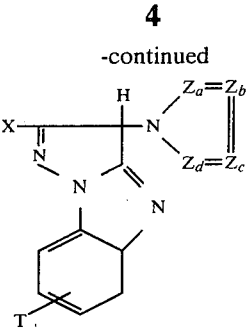

In the above general formulae, W represents a hydrogen atom; or has up to 40 carbon atoms, preferably up to 22 carbon atoms. Suitable examples of groups for W include a straight chain or branched chain alkyl group (e.g., a methyl, ethyl, isopropyl, tert-butyl, hexyl, dodecyl, docosyl, etc., group), an alkenyl group (e.g., an allyl, β-vinylethyl, etc., group), a cycloalkyl group (e.g., a cyclohexyl, norbornyl, 7,7-dialkylnorbornyl, 2-pentadecyl-7,7-dialkylnorbornyl, etc., group), an aralkyl group (e.g., a benzyl, β-phenylethyl, etc., group) or a cycloalkenyl group (e.g., a cyclopentenyl, cyclohexenyl, etc., group) and these groups as described above can be substituted with one or more of a halogen atom (e.g., a chlorine, bromine, fluorine, etc., atom), a nitro group, a cyano group, an aryl group (e.g., phenyl, tolyl, methoxyphenyl, naphthyl, etc., group), an alkoxy group (e.g., a methoxy, butoxy, octyloxy, etc., group), an aryloxy group (e.g., a phenoxy, tolyloxy, naphthoxy, etc., group), a carboxyl group, an alkylcarbonyl group (e.g., a methylcarbonyl, octylcarbonyl, etc., group), an arylcarbonyl group (e.g., a phenylcarbonyl, tolylcarbonyl, etc., group), an alkoxycarbonyl group (e.g., a methoxycarbonyl, butoxycarbonyl, etc., group), an aryloxycarbonyl group (e.g., a phenoxycarbonyl, tolyloxycarbonyl, etc., group), a sulfo group, an acyloxy group (e.g., an acetyl group, etc.), a sulfamoyl group (e.g., an N-methylsulfamoyl, N,N-diethylsufamoyl, N-methyl-N-phenylsulfamoyl, etc., group), a carbamoyl group (e.g., an N-ethylcarbamoyl, N-methyl-N-decylcarbamoyl, N-phenylcarbamoyl, etc., group), an acylamino group (e.g., an acetamido, butyramido, benzamido, etc., group), a diacylamino group (e.g., a phthalimido, 3-heptadecylsuccinimido, etc., group), a ureido group (e.g., an ethylureido, phenylureido, chlorophenylureido, etc., group), a thioureido group (e.g., an ethylthioureido, phenylthioureido, chlorophenylthioureido, etc., group), an alkoxycarbonylamino group (e.g., a methoxycarbonylamino, octoxycarbonylamino, etc., group), an aryloxycarbonylamino group (e.g., a phenoxycarbonylamino group, etc.), an alkoxythiocarbonylamino group (e.g., a methoxythiocarbonylamino, octoxythiocarbonylamino, etc., group), an aryloxythiocarbonylamino group (e.g., a phenoxythiocarbonylamino group, etc.), a sulfonamido group (such as an alkylsulfonamido (e.g., methylsulfonamido, ethylsulfonamido, etc.), arylsulfonamido (e.g., phenylsulfonamido, etc., group), a heterocyclic group (e.g., a 5- or 6-membered heterocyclic group or condensed heterocyclic group containing at least one hetero atom selected from nitrogen, oxygen and sulfur atoms, such as a furyl, oxazolyl, benzothiazolyl, imidazolyl, etc., group), an arylsulfonyloxy group (e.g., a phenylsulfonyloxy, tolylsulfonyloxy, etc., group), an alkylsulfonyloxy group (e.g., an ethylsulfonyloxy, dodecylsulfonyloxy, etc., group), an arylsulfonyl group (e.g., a phenylsulfonyl, tolylsulfonyl, etc., group), an alkylsulfonyl group (e.g., a methylsulfonyl, octylsulfonyl, etc., group), an arylthio group (e.g., a phenylthio, tolylthio, etc., group), an alkylthio group (e.g., a methylthio, octylthio, dodecylthio, etc., group), an alkylsulfinyl group (e.g., a methylsulfinyl, hexylsulfinyl, etc., group), an arylsulfinyl group (e.g., a phenylsulfinyl, tolylsulfinyl, etc., group), an alkylamino group (e.g., a methylamino, butylamino, etc., group), an dialkylamino group (e.g., an N,N-diethylamino, N-methyl-N-decylamino, etc., group), an anilino group (such as an N-alkylanilino (e.g., N-methylanilino etc.), N-arylanilino (e.g., N-phenylanilino etc.), N-acylanilino (e.g., 2-chloro-5-tetradecanamidoanilino, etc.), etc., group), a hydroxyl group, or a mercapto group.

Furthermore W represents an aryl group (e.g., a phenyl or an α- or β-naphthyl group) or an aryl group having one or more substituents such as an alkyl group (e.g., a methyl, ethyl, octyl, etc., group), an alkenyl group (e.g., an allyl, β-vinylethyl, etc., group), a cycloalkyl group (e.g., a cyclohexyl, norbornyl, 7,7-dialkylnorbornyl, 2-pentadecyl-7,7-dialkylnorbornyl, etc., group), an aralkyl group (e.g., a benzyl, β-phenylethyl, etc., group), an cycloalkenyl group (e.g., a cyclopentenyl, cyclohexenyl, etc., group), a halogen atom (e.g., a chlorine, bromine, fluorine, etc., atom), a nitro group, a cyano group, an aryl group (e.g., a phenyl, tolyl, methoxyphenyl, naphthyl, etc., group), an alkoxy group e.g., a methoxy, butoxy, octyloxy, etc., group), an aryloxy group (e.g., a phenoxy, tolyloxy, naphthoxy, etc., group), a carboxy group, an alkylcarbonyl group (e.g., a methylcarbonyl, octylcarbonyl, etc., group), an arylcarbonyl group (e.g., a phenylcarbonyl, tolylcarbonyl, etc., group), an alkoxycarbonyl group (e.g., a methoxycarbonyl, butoxycarbonyl, etc., group), an aryloxycarbonyl group (e.g., a phenoxycarbonyl, tolyloxycarbonyl, etc., group), a sulfo group, an acyloxy group (e.g., an acetoxy, etc., group), sulfamoyl group (e.g., a methylsulfamoyl, diethylsulfamoyl, phenylsulfamoyl, etc., group), a carbamoyl group (e.g., a carbamoyl, N-octadecylcarbamoyl, N,N-dihexylcarbamoyl, N-methyl-N-phenylcarbamoyl, 3-pentadecylphenylcarbamoyl, etc., group), an acylamino group (e.g., an acetamido, butyramido, benzamido, etc., group), a diacylamino group (e.g., a succinimido, phthalimido, hydantoinyl, etc., group), a ureido group (e.g., an ethylureido, phenylureido, chlorophenylureido, etc., group), a thioureido group (e.g., an ethylthioureido, phenylthioureido, chlorophenylthioureido, etc., group), an alkoxycarbonylamino group (e.g., a methoxycarbonylamino, octoxycarbonylamino, etc., group), an aryloxycarbonylamino group (e.g., a phenyloxycarbonylamino etc., group), an alkoxythiocarbonylamino group (e.g., a methoxythiocarbonylamino, octoxythiocarbonylamino, etc., group), an aryloxythiocarbonylamino group (e.g., a phenoxythiocarbonylamino group, etc.), a sulfonamido group (such as an alkylsulfonamido (e.g., methylsulfonamido, ethylsulfonamido, etc.), arylsulfonamido (e.g., phenylsulfonamido, etc.,) etc., group), a heterocyclic group (e.g., a 5- or 6-membered heterocyclic group or condensed heterocyclic group containing at least one hetero atom selected from nitrogen, oxygen and sulfur atoms, such as a furyl, oxazolyl, benzothiazolyl, imidazolyl, etc., group), an arylsulfonyloxy group, (e.g., a phenylsulfonyloxy, tolylsulfonyloxy etc., group), an alkylsulfonyloxy group, (e.g., an ethylsulfonyloxy, dodecylsulfonyloxy, etc., group), an arylsulfonyl group, (e.g., a phenylsulfonyl, tolysulfouyl, etc., group), an alkylsulfonyl group (e.g., a methylsulfonyl, octylsulfonyl, etc., group), an arylthio group (e.g., phenylthio, tolylthio, etc., group), an alkylthio group, (e.g., a methylthio, octylthio, dodecylthio, etc., group), an alkylsulfinyl group, (e.g., a methylsulfinyl, hexylsulfinyl, etc., group), an arylsulfinyl group, (e.g., a phenylsulfinyl, tollylsulfinyl, etc., group), an alkylamino group (e.g., a methylamino, butylamino, etc., group), a dialkylamino group, (e.g., an N,N-diethylamino, N-methyl-N-decylamino, etc., group), an anilino group, an N-alkylanilino group (e.g., an N-methylanilino group, etc.), an N-arylanilino group (e.g., an N-phenylanilino group, etc.), an N-acylanilino group (e.g., a 2-chloro-5-tetra-decanamidoanilino group), etc., a hydroxyl group, and a mercapto group. More preferably W is a phenyl group substituted with an alkyl group, an alkoxy group, or a halogen atom in at least one of the ortho positions because in such case the coupler remaining in the processed photographic film causes less print out due to the action of heat and light.

Still further, W represents also a heterocyclic group (e.g., a 5-membered or 6-membered heterocyclic group containing a nitrogen atom (for example, a pyridyl, quinolyl or pyrrolyl group, which may be substituted with a substituent as described above for the aryl group of W), or two or more nitrogen atoms (for example, a pyrazolyl, benzotriazolyl, tetrazolyl, etc., group), an oxygen atom (for example, an unsubstituted or substituted furyl or benzofuranyl group having a substituent described above for the aryl group of W); a sulfur atom (for example, an unsubstituted or substituted thienyl or benzo(b)thienyl group having a substituent as described above for the aryl group of W); and a heterocyclic group containing two or more different hetero-atoms (such as benzoazolyl, benzothiazolyl, and the like).

Moreover, W represents further an acyl group (such as an alkylcarbonyl group (e.g., an acetyl, butyryl, benzoyl, etc., group), a thioacyl group (such as an alkylthiocarbonyl group (e.g., an octylthiocarbonyl, etc., group), an alkylsulfonyl group (e.g., a methylsulfonyl, octylsulfonyl, etc., group), an arylsulfonyl group (e.g., a phenylsulfonyl, tolylsulfonyl, etc., group)), an alkylsulfinyl group (e.g., a methylsulfinyl, hexylsulfinyl, etc., group), an arylsulfinyl group, (e.g., a phenylsulfinyl, tolylsulfinyl, etc., group), a carbamoyl group (such as an alkylcarbamoyl, dialkylcarbamoyl, arylcarbamoyl, etc., (e.g., N-ethylcarbamoyl, N-methyl-N-decylcarbamoyl, phenylcarbamoyl, etc.) etc., group), or a thiocarbamoyl group (such as an alkylthiocarbamoyl (e.g., ethylthiocarbamoyl, etc.), dialkylthiocarbamoyl (e.g., N-methyl-N-decylthiocarbamoyl, etc.), arylthiocarbamoyl (e.g., phenylthiocarbamoyl, etc.) etc., group).

In the above described formulae, X represents a hydrogen atom, or has up to 40, preferably up to 22, carbon atoms. Suitable examples of groups for X include an alkyl group, an alkenyl group, a cycloalkyl group, an aralkyl group, or a cycloalkenyl group as defined for W, and these groups may be substituted with one or more substituents as illustrated above in regard to these groups of W.

Furthermore, X represents also an aryl group as defined for W or a heterocyclic group as defined for W, each of which may also have one or more of the substituents as illustrated above for W.

Still further, X represents an alkoxycarbonyl group (e.g., a methoxycarbonyl, ethoxycarbonyl, stearyloxycarbonyl, etc., group), an aryloxycarbonyl group (e.g., a phenoxycarbonyl α-naphthoxycarbonyl, β-naphthoxycarbonyl, etc., group), an aralkoxycarbonyl group (e.g., a benzyloxycarbonyl etc., group), an alkoxy group (e.g., a methoxy, ethoxy, decyloxy, etc., group), an aryloxy group (e.g., a phenoxy, tolyloxy, etc., group), an alkylthio group (e.g., an ethylthio, dodecylthio, etc., group), an arylthio group (e.g., a phenylthio, β-naphthylthio etc., group), a carboxyl group, an acylamino group (e.g., an acetamido, 3-[(2,4-di-tert-amylphenoxy)acetamido]benzamido, etc., group), a diacylamino group (e.g., a phthalimido, 3-heptadecylsuccinimido, etc., group), an N-alkylacylamino group (e.g., an N-methylpropionamido, etc. group), an N-acylacylamino group (e.g., an N-phenylacetamido, etc., group), a ureido group (such as a ureido), N-arylureido (e.g., N-phenylureido, etc.), N-alkylureido (e.g., N-ethylureido, etc.), etc., group) a thioureido group (such as a thioureido, N-arylthioureido (e.g., N-phenylthioureido, etc.), N-alkylthioureido (e.g., N-ethylthioureido, etc.), etc. group), an alkoxycarbonylamino group (e.g., a methoxycarbonylamino, octoxycarbonylamino, etc., group), an aryloxycarbonylamino group (e.g., a phenoxycarbonylamino group, etc.), an alkoxythiocarbonylamino group (e.g., a methoxythiocarbonylamino, octoxythiocarbonylamino, etc., group), an aryloxythiocarbonylamino group (e.g., a phenoxythiocarbonylamino, etc., group), an anilino group (e.g., a phenylamino, 2-chloro-5-tetradecanamidoanilino, etc. group), an N-alkylanilino group (e.g., an N-methylanilino, etc., group), an N-arylanilino group (e.g., an N-phenylanilino, etc., group), an N-acylanilino group (e.g., an N-acetyl-2-chloro-5-tetradecyloxycarbonylanilino, etc., group), an N-alkylamino group (e.g., an N-butylamino, N-methylamino, etc., group), an N,N-dialkylamino group (e.g., an N,N-dibutylamino, etc., group), an N-cycloalkylamino group (e.g., an N-cyclohexylamino, etc., group), a cycloamino group (e.g., a piperidino, pyrrolidino, etc., group), a heterocyclic amino group (e.g., a 2-oxazolylamino, 2-thiazolylamino, etc., group), an N-alkyl-N-heterocyclic amino group (e.g., an N-methyl-N-(2-oxazolyl)amino, N-ethyl-N-(2-pyridyl)amino etc., group), an N-aryl-N-heterocyclic amino group (e.g., an N-phenyl-N-(2-pyridyl)amino, etc., group), an N-acylamino-N-heterocyclic amino group (e.g., an N-acetyl-N-(2-benzimidazolyl)amino, etc., group), an alkylcarbonyl group (e.g., a methylcarbonyl, etc., group), an arylcarbonyl group (e.g., a phenylcarbonyl, etc., group), a sulfonamido group (such as an alkylsulfonamido (e.g., methylsulfonamido, etc.), arylsulfonamido (e.g., phenylsulfonamido, etc.) etc., group), a carbamoyl group (such as an N-alkylcarbamoyl group (e.g., N-methylcarbamoyl, N-{3-[(2,4-di-tert-amylphenoxy)acetamido]phenyl}carbamoyl, etc.), N,N-dialkylcarbamoyl (e.g., N-methyl-N-octadecylcarbamoyl, etc.), N-alkyl-N-arylcarbamoyl (e.g., an N-methyl-N-phenylcarbamoyl, etc.,), N,N-diarylcarbamoyl (e.g., N,N-diphenylcarbamoyl etc.) etc., group), a sulfamoyl group (such as an N-alkylsulfamoyl (e.g., N-methylsulfamoyl), N-{3-[(2,4-di-tert-amylphenoxy)acetamido]benzyl}sulfamoyl, etc.,), N,N-dialkylsulfamoyl (e.g., N-methyl-N-octadecylsulfamoyl, etc.), N-arylsulfamoyl group (e.g., N-phenylsulfamoyl, etc.), N-alkyl-N-arylsulfamoyl (e.g., N-methyl-N-phenylsulfamoyl, etc.), N,N-diarylsulfamoyl (e.g., N,N-diphenylsulfamoyl etc.) etc., group) a guanidino group (such as an N-alkylguanidino (e.g., N-methylguanidino, etc.), N-arylguanidino (e.g., N-phenylguanidino, etc.) etc., group), a cyano group, an acyloxy group (e.g., a tetradecanoyloxy, etc., group), a sulfonyloxy group (e.g., a benzenesulfonyloxy etc., group), a hydroxyl group, a mercapto group, a halogen atom (e.g., a chlorine, bromine, fluorine, etc., atom), or a sulfo group.

In the above-described formulae, T represents a hydrogen atom, or has up to 40, preferably up to 22, carbon atoms. Suitable examples of groups for T include a straight chain or branched chain alkyl group, an alkenyl group, a cycloalkyl group, an aralkyl group, or a cycloalkenyl group as defined for W, in which the groups may have one or more substituents as illustrated above in regard to these groups of W.

Furthermore, T represents also an aryl group or a heterocyclic group, each as defined for W, in which each of these groups may have one or more substituents as described above in regard to W.

Still further, T represents a cyano group, a thiocyano group, an alkoxy group (e.g., a methoxy, butoxy, octyloxy, etc., group), an aryloxy group (e.g., a phenoxy, tolyloxy, naphthoxy, etc., group), a halogen atom (e.g., a chlorine, bromine, fluorine, etc., atom), a carboxyl group, an alkoxycarbonyl group (e.g., a methoxycarbonyl, butoxycarbonyl, etc., group), an aryloxycarbonyl group, (e.g., a phenoxycarbonyl, tolyloxycarbonyl, etc., group), an acyloxy group (e.g., an acetoxy, etc., group), an alkylcarbonyl group (e.g., a methylcarbonyl, octylcarbonyl, etc., group), an arylcarbonyl group (e.g., a phenylcarbonyl, tolylcarbonyl, et., group), a thioacyl group (such as an alkylthiocarbonyl group (e.g., an ethylthiocarbonyl etc., group), an arylthiocarbonyl group (e.g., a phenylthiocarbonyl, etc., group), a sulfo group, a sulfamoyl group (e.g., a methylsulfamoyl, diethylsulfamoyl, phenylsulfamoyl, etc., group), a carbamoyl group (such as an alkylcarbamoyl, dialkylcarbamoyl, arylcarbamoyl, etc. group, (e.g., N-ethylcarbamoyl, N-methyl-N-decylcarbamoyl, N-phenylcarbamoyl, etc, group), an acylamino group (e.g., an acetamido, butyramido, benzamido, etc., group), a diacylamino group (e.g., a phthalimido, 3-heptadecylsuccinimido, etc., group), a ureido group (e.g., an ethylureido, phenylureido, chlorophenylureido, etc., group), a thioureido group (e.g., an ethylthioureido, phenylthioureido, chlorophenylthioureido, etc., group), an alkoxycarbonylamino group (e.g., a methoxycarbonylamino, octoxycarbonylamino etc., group), an aryloxycarbonylamino group (e.g., a phenoxycarbonylamino etc., group), an alkoxythiocarbonylamino group (e.g., a methoxythiocarbonylamino, octoxythiocarbonylamino, etc., group), an aryloxythiocarbonylamino group (e.g., a phenoxythiocarbonylamino, etc., group), a sulfonamido group (such as an alkylsulfonamido (e.g., methylsulfonamido, ethylsulfonamido, etc.), arylsulfonamido (e.g., phenylsulfonamido, etc.) etc., group), an alkylsulfonyloxy group (e.g., an ethylsulfonyloxy, dodecylsulfonyloxy, etc., group), an arylsulfonyloxy group (e.g., a phenylsulfonyloxy, tolylsulfonyloxy, etc., group), an arylsulfonyl group (e.g., a phenylsulfonyl, tolylsulfonyl, etc., group), an alkylsulfonyl group (e.g., a methylsulfonyl, octylsulfonyl, etc., group), an arylthio group (e.g., a phenylthio, tolylthio, etc., group), an alkylthio group (e.g., a methylthio, octylthio, dodecylthio, etc., group), an alkylsulfinyl group (e.g., a phenylsulfinyl, tolylsulfinyl, etc., group), an alkylamino group (e.g., a methylamino, butylamino, etc., group), a dialkylamino group (e.g., an N,N-diethylamino, N-methyl-N-decylamino, etc., group), an anilino group, an N-arylanilino group (e.g., an N-phenylanilino, etc., group), an N-alkylanilino group (e.g., an N-methylanilino, etc., group), an N-acylanilino group (e.g., a 2-chloro-5-tetradecanamidoanilino etc., group), a hydroxyl group, or a mercapto group.

In the above general formulae, $Z_a$, $Z_b$, $Z_c$ and $Z_d$ in the

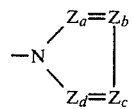

moiety, which may be the same or different, each represents a methine group, (for example, an unsubstituted methine group or a substituted methine group) substituted with a substituent having up to 40 carbon atoms, preferably up to 22 carbon atoms, e.g., a straight or branched chain alkyl group (e.g., a methyl, ethyl, isopropyl, tert-butyl, hexyl, octyl, dodecyl, docosyl, etc. group), an alkenyl group (e.g., an allyl, β-vinylethyl, etc. group), a cycloalkyl group (e.g., a cyclohexyl, norbornyl, 7,7-dialkylnorbornyl, 2-pentadecyl-7, 7-dialkyl-norbornyl, etc., group), an aralkyl group (e.g., a benzyl, β-phenylethyl, etc., group), a cycloalkenyl group (e.g., a cyclopentenyl, cyclohexenyl, etc., group) an aryl group (e.g., a phenyl, tolyl, methoxyphenyl, α or β-naphthyl, etc., group), a heterocyclic group (e.g., a 5-membered or 6-membered heterocyclic group containing a nitrogen atom (for example, a pyridyl, quinolyl or pyrrolyl group, which can be substituted with a substituent as described above for the aryl group), two or more nitrogen atoms (for example, a pyrazolyl, benzotriazolyl, tertazolyl, etc., group), an oxygen atom (for example, an unsubstituted or substituted furyl or benzofuranyl group having a substituent as described above for the aryl group); a sulfur atom (for example, an unsubstituted or substituted thienyl or benzo[b]thienyl group having a substituent as described above for the aryl group); and a heterocyclic group containing two or more different hetero-atoms (such as a benzoazolyl, benzothiazolyl, etc. group); an alkoxycarbonyl group (e.g., a methoxycarbonyl, ethoxycarbonyl, butoxycarbonyl, octadecyloxycarbonyl, etc. group), an aryloxycarbonyl group, (e.g., a phenyoxycarbonyl, α- or β-naphthoxycarbonyl, tolyloxycarbonyl, etc. group), an aralkyloxycarbonyl group (e.g., a benzyloxycarbonyl, etc. group), an alkoxy group (e.g., a methoxy, butoxy, octyloxy, decyloxy, etc. group), an aryloxy group (e.g., a phenoxy, tolyloxy, naphthoxy, etc. group), an alkylthio groups (e.g., a methylthio, etc., group), a carboxy group, an acylamino group (e.g., an acetamido, butyramido, benzamido, 3-[(2,4-di-tert-amylphenoxy)-acetamido]benzamido, etc., group), a diacylamino group (e.g., a phthalimido, 3-heptadecylsuccimimido, hydantoinyl, etc. group), an N-alkylacylamino group (e.g., an N-methylpropionamido, etc. group), an N-arylacylamino group (e.g., a N-phenylacetamido, etc. group), a ureido group (e.g., a ureido, ethylureido, phenylureido, chlorophenylureido, etc. group), a thioureido group (e.g., an ethylthioureido, phenylthioureido, chlorophenylthioureido, etc. group), an alkoxycarbonylamino group (e.g., a methoxycarbonylamino, octoxycarbonylamino, etc. group), an aryloxycarbonylamino group (e.g., a phenoxycarbonylamino, tolyloxycarbonylamino, etc. group), an alkoxy(thiocarbonyl)amino group (e.g., a methoxy(thiocarbonyl)amino, octoxy(thiocarbonyl)amino, etc. group), an aryloxy(thiocarbonyl)amino (e.g., a phenoxy(thiocarbonyl)amido, tolyloxy(thiocarbonyl)amino, etc. group), an anilino group, an alkylamino group (eg., an N-butylamino, N-methylamino, an N,N-dibutylamino, N,N-diethylamino, N-methyl-N-decylamino, etc. group), a cycloamino group (e.g., a piperidino, pyrrolidino, etc. group), an alkylcarbonyl group (e.g., an acetyl, butyryl, benzoyl, etc. group), an arylcarbonyl group (e.g, a phenylcarbonyl, tolylcarbonyl, etc. group), a sulfonamido group (such as an alkylsulfonamido (e.g., methylsulfonamido, etc.), arylsulfonamido (e.g., phenylsulfonamido, etc.) etc., group, a carbamoyl group (such as an N-alkylcarbamoyl group (e.g., N-methylcarbamoyl, N-{3-[2,4-di-tert-amylphenoxy)acetamido]benzyl}carbamoyl, etc.), N,N-dialkylcarbamoyl (e.g., N-methyl-N-octadecylcarbamoyl, etc.), N-alkyl-N-arylcarbamoyl (e.g., an N-methyl-N-phenylcarbamoyl, etc.). etc., group), a sulfamoyl group (such as an N-alkylsulfamoyl (e.g., N-methylsulfamoyl, N-{3-[(2,4-di-tert-amylphenoxy)acetamido]benzyl}sulfamoyl, etc.,), N-N-dialkylsulfamoyl (e.g., N-methyl-N-octadecylsulfamoyl, etc.), N-arylsulfamoyl group (e.g., N-phenylsulfamoyl, etc.), N-alkyl-N-arylsulfamoyl (e.g., N-methyl-N-phenylsulfamoyl, etc.), N,N-diarylsulfamoyl (e.g., N,N-diphenylsulfamoyl, etc.) etc., group), a cyano group, an acyloxy group (e.g., an acetoxy, tetradecanoyloxy, etc. group), a sulfonyloxy group (such as an arylsulfonyloxy) (e.g., a phenylsulfonyloxy, tolylsulfonyloxy, etc.), alkylsulfonyloxy (e.g., ethylsulfonyloxy, dedcylsulfonyloxy, etc.), etc. group), a halogen atom (e.g., a chlorine, bromine, fluorine, etc. atom), a sulfo group, or a nitro group), or an —N═- group, and the nitrogen-containing ring formed by $Z_a$, $Z_b$, $Z_c$ and $Z_d$ can further form a mono- or bi-cyclic fused ring therewith (e.g., a 5- or 6-membered ring containing two adjacent $Z_a$ to $Z_d$ moieties, preferably a hydrocarbyl ring such as a cyclohexene ring, cyclopentene ring, or the like, a hetero cyclic ring such as a dihydrofuran ring, a dihydrothiophene ring, etc., which can be substituted with one or more of the substituents as illustrated above for the substituted methine group).

$Z_a$ to $Z_d$ do not form a benzotriazolyl-1, benzotriazolyl-2, benzyimidazolyl-1 or indazolyl-1 group. Further, particularly preferable couplers of the present invention are those represented by the general formulae (II) and (III), wherein (1) $Z_a$, $Z_b$, $Z_c$ and $Z_d$ of

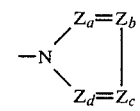

moiety, each represents a methine group (both unsubstituted and substituted as described above) and an —N═ group to form a monocyclic, nitrogen-containing, aromatic 5-membered heterocyclic group, or (2) the

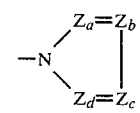

moiety represents a

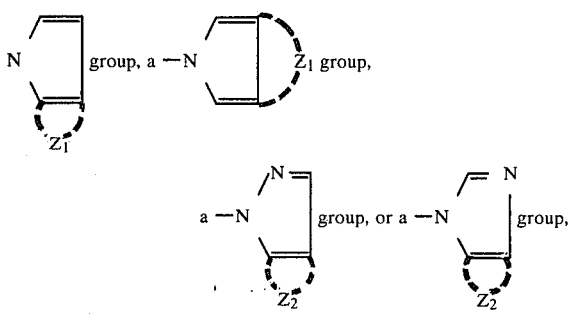

where $Z_1$ represents the group of atoms necessary to form a 5- or 6-membered hydrocarbyl or heterocyclic ring and $Z_2$ represents the group of atoms necessary to form a 5- or 6-membered non-aromatic hydrocarbyl ring, a 5- or 6-membered non-aromatic heterocyclic ring containing a nitrogen atom as a hetero atom, or a 5- or 6-membered heterocyclic ring containing a hetero atom selected from the group consisting of an oxygen atom and a sulfur atom. Examples of the rings formed by $Z_1$ and $Z_2$ are monocyclic fused ring such as a hydrocarbyl ring (e.g., a pentene, benzene etc., ring and a heterocyclic ring (e.g., a pyridine, pyrimidine, 2-oxopyrimidine, dihydrofuran, dihydrothiophene, etc., ring) which can be substituted with one or more of the substituents as defined above for the methine group; or a bicyclic fused ring (e.g., a naphthalene, quinoline, etc., ring).

The

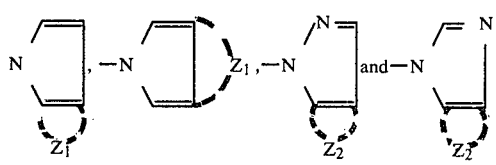

can be substituted with a substituent as described above for the substituted methine group. Further, specific examples of 5- or 6-membered fused ring moiety formed by $Z_1$ and $Z_2$ are the same as described above with respect to the hydrocarbyl and heterocyclic rings for the general formulae (II) and (III).

Preferred examples of nitrogen-containing heterocyclic groups represented by

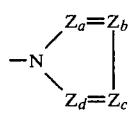

moiety include e.g., the following groups: a 1-imidazolyl group, a 2-methyl-1-imidazolyl group, a 2-methylthio-1-imidazolyl group, a 2-ethylthio-1-imidazolyl group, a 2,4-dimethyl-1-imidazoyl group, a 4-methyl-1-imidazolyl group, a 4-nitro-1-imidazolyl group, 2-phenyl-1-imidazolyl group, a 4-chloro-1-imidazolyl group, a 4-phenyl-1-imidazolyl group, a 4-acetyl-1-imidazolyl group, a 4-tetradecanamido-1-imidazolyl group, a 1-pyrrolyl group, a 3,4-dichloro-1-pyrrolyl group, a 2-isoindolyl group, a 1-indolyl group, a 1-pyrazolyl group, a 2-indazolyl group, a 1,2,4,4-triazolyl group, a 1,2,3-1-triazolyl group, a 1-tetrazolyl group, 3,3-dimethyl-1,2,4-1-triazolyl group, a 3,5-diethyl-1,2,4-1-triazolyl group, a 7-xanthinyl group, a 7-hypoxanthinyl group.

The coupler of the present invention represented by the general formulae (II) and (III) can be combined directly or through a W, X, T, $Z_a$, $Z_b$, $Z_c$ and $Z_d$ divalent group to form a symmetrical or an asymmetrical complex coupler.

The magenta couplers of the present invention provide various properties depending upon the particular W, X, T, $Z_a$, $Z_b$, $Z_c$ and $Z_d$ substituents and can be employed for various photographic purposes. When at least one of W, X and T contains a hydrophobic residue having 8 or more carbon atoms, the coupler associates in a hydrophilic colloid to become non-diffusible in a hydrophilic colloidal layer of a light-sensitive material. Such a coupler can be incorporated in a silver halide emulsion layer. Couplers having a diffusion-resistant hydrophobic residue in $Z_a$, $Z_b$, $Z_c$ or $Z_d$ and containing a water-solubilizing group such as a sulfo group or a carboxy group in at least one of W, X and T provide a diffusible dye through an oxidative coupling reaction with an aromatic primary amine developing agent, although the couplers themselves are non-diffusible. Such couplers which are capable of providing diffusible dyes are useful for diffusion transfer color photography.

The process of forming dye images through oxidative coupling reaction with an aromatic primary amine developing agent can be classified into two types depending on the manner of adding the couplers; one type being a so-called incorporated-coupler type wherein couplers are incorporated in an emulsion during the production of a light-sensitive material; and the other type being a so-called non-incorporated coupler type wherein couplers are dissolved in a developer and are supplied, upon development, through diffusion into an emulsion layer.

Couplers for use in the incorporated-coupler type system must be immobilized in an emulsion layer, i.e., must be made diffusion-resistant. Otherwise, couplers would migrate through a light-sensitive material to form a color in the wrong emulsion layer having a different sensitivity, thus seriously degrading the color reproducibility of the light-sensitive material.

In order to render the couplers diffusion-resistant, a group having a hydrophobic residue containing 8 to 32 carbon atoms is introduced into the coupler molecule. Such a residue is called a ballasting group. This ballasting group can be connected to the coupler skeletal structure directly or through an imino bond, an ether bond, a carbonamido bond, a sulfonamido bond, ureido bond, an ester bond, an imido bond, a carbamoyl bond, a sulfamoyl bond, or the like.

Several specific examples of the ballasting group are as described in the specific examples of the couplers of the present invetion.

Typical examples of the ballasting groups include, e.g., an alkyl group, an alkoxyalkyl group, an alkenyl group, an aryl group substituted by an alkyl group, an aryl group substituted by an alkoxy group, an terphenyl group, and the like. These ballasting groups may be substituted by, for example, a halogen atom (e.g., fluorine, chlorine, etc.), a nitro group, a cyano group, an alkoxycarbonyl group, an amido group, a carbamoyl group, a sulfonamido group, etc. Specific examples of the ballasting group include an n-octyl group, a 2-ethylhexyl group, a tert-octyl group, an n-nonyl group, an n-decyl group, an n-dodecyl group, a 1,1-dimethyldecyl group, a 2,2-dimethyldecyl group, an n-octadecyl group, a 2-(n-hexyl)decyl group, an n-octadecyl group, a 9,10-dichlorooctadecyl group, a heptyloxyethyl group, a 2,4-di-tert-amylcyclohexyldodecyloxypropyl group, an oleyl group, a 2,4-di-tert-butylphenyl group, a 2,4-di-tert-amylphenyl group, a 2,4-di-tert-amyl-6-chlorophenyl group, a 3-n-pentadecylphenyl group, a 2-dodecyloxyphenyl group, a 3-heptadecyloxyphenyl group, an o-terphenyl group, a perfluoroheptyl group, etc.

Specific examples of ballast groups are illustrated below (I). Alkyl groups and alkenyl groups:
For instance, $-CH_2-CH(C_2H_5)$, $-C_{12}H_{25}$, $-C_{16}H_{33}$, $-C_{17}H_{35}$, etc.

(II). Alkoxyalkyl groups:
For instance, $-(CH_2)_3-O-(CH_2)_7CH_3$, $$-(CH_2)_3OCH_2-\underset{C_2H_5}{CH}-(CH_2)_8-CH_3,$$

etc., as described in Japanese Patent Publication No. 27563/1964.

(III). Alkylaryl groups:
For instance,

[structures of alkylaryl groups with $C_9H_{19}$, $C_4H_9(t)$ substituents]

(IV). Alkylaryloxyalkyl groups:
For instance,

[structures with $-CH_2O-$, $-(CH_2)_3O-$ linkages to phenyl rings bearing $C_5H_{11}(t)$, $C_5H_{11}(sec)$ substituents, and $-CHO-$ with $C_2H_5$ side chain]

(V). Acylamidoalkyl groups:

For instance, $$-CH_2CH_2N\begin{matrix}COC_{15}H_{31}\\ C_4H_9\end{matrix}, \quad -CH_2CH_2N\begin{matrix}COC_{13}H_{27}\\ C_3H_7\end{matrix},$$

$$-CH_2CH_2NHCOCH_2CH_2N\begin{matrix}COC_{13}H_{27}\\ C_3H_7\end{matrix}, \text{ etc.,}$$

as described in U.S. Pat. No. 3,337,344 and 3,418,129.

(VI). Alkoxyaryl groups and aryloxyaryl groups:
For instance,

[phenyl-$OC_{13}H_{27}(n)$], [phenyl-O-phenyl-$C_{12}H_{25}(n)$], etc.

(VII). Residues having a long chain alkyl or alkenyl aliphatic group and also a carboxyl or sulfo water-solubilizing group:
For instance, $$-\underset{CH_2COOH}{CH}-CH=CH-C_{16}H_{33}, \quad -\underset{SO_3H}{CH}-C_{16}H_{33}, \text{ etc.}$$

(VIII). Alkyl groups substituted with an ester group:
For instance, $$-\underset{COOC_2H_5}{CH}-C_{16}H_{33}(n),$$

$-CH_2-CH_2-COOC_{12}H_{25}(n)$, etc.

(IX). Alkyl groups substituted with an aryl group or a heterocyclic group: For instance, $$-CH_2-CH_2-\text{phenyl}-NHCOCH_2\underset{COOCH_3}{CH}-C_{18}H_{37}(n),$$

[structure with $-CH_2CH_2-$ phenyl-N-heterocycle with $C_{18}H_{37}(n)$], etc.

(X). Aryl groups substituted with an aryloxyalkoxycarbonyl group:
For instance,

[phenyl-$COOCH_2\underset{C_2H_5}{CHO}-$ phenyl with $C_5H_{11}(t)$ substituents], etc.

The couplers of the present invention in which the coupling position is substituted by a nitrogen-containing aromatic heterocyclic ring at the nitrogen position thereof can be produced, in general, according to the following reaction schematic:

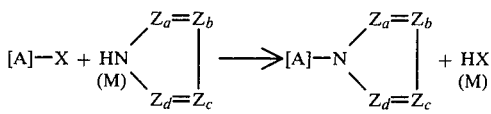

wherein [A], $Z_a$, $Z_b$, $Z_c$ and $Z_d$ are each as described above, X is a halogen atom (e.g., a chlorine atom, a bromine atom, etc.) substituted in the coupling position of the magenta coupler and (M) is a metal atom, by reacting a magenta coupler of the formula [A]-X having a halogen atom in the coupling position with a nitrogen-containing heterocyclic ring compound of the formula

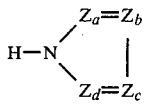

or with a salt of a nitrogen-containing aromatic heterocyclic ring compound of the formula

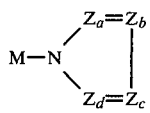

[e.g., a metal salt (e.g., M represents sodium, potassium, silver, magnesium, lithium, etc.) or a basic quaternary salt (e.g., M represents a triethylammonium ion, etc.)]. The N-containing heterocyclic ring compound can be employed in an amount of about 1 to 10 moles preferably about 2 to 4 moles, per mole of the magenta coupler of the formula [A]-X. The coupler [A]-X wherein such is an unsubstituted 5-pyrazolones can be synthesized according to the process described in, e.g., U.S. Pat. Nos. 3,006,759 and 3,522,051. Also, when an electron-donating group such as an anilino group is substituted in the 3-position of a 5-pyrazolone, the mono-halo-substituted couplers can be synthesized with ease by converting the coupler to a 3-N-alkoxycarbonyl-anilino-5-pyrazolone derivative, a 3-N-acetylanilino-5-pyrazolone derivative or a 3-N-trichloroacetyl-anilino-5-pyrazolone derivative, and halogenating the resulting 3-substituted coupler. This step of halogenating the coupler is illustrated in the Synthesis Examples described hereinafter. With pyrazolobenzimidazole type magenta couplers, the mono-halo-substitution in the coupling position is possible in the same manner as above. The reaction between the thus produced [A]-X and a nitrogen-containing aromatic heterocyclic ring compound can be effected at a temperature of from about 0° C. to 200° C. in various solvents or in the absence of a solvent by melting the reactants. Preferred temperatures range from about 20° C. to 150° C. and, where the reactants are reacted by melting, the temperature needs to be no higher than the melting point as long as both reactants are soluble at that temperature. Illustrative preferred solvents include alcoholic solvents (e.g., methanol, ethanol, propanol, etc.), aromatic solvents (e.g., benzene, toluene, xylene, etc.), aprotic polar solvents (e.g., dimethylformamide, hexamethylphosphotriamide, etc.), and the like.

In the reaction between a nitrogen-containing aromatic heterocyclic ring compound having an electron pair on the nitrogen atom in the ring thereof such as a diazole, triazole, tetrazole, etc. ring and [A]-X, it is not necessary to use the heterocyclic ring compounds as a metal salt since the heterocyclic ring compounds can be used as a dehydrohalogenating agent. In such case, the synthesis can be accomplished using the heterocyclic ring compounds in an excess amount of two to four equivalents to the [A]-X compound. Introduction of a pyrrole ring of nitrogen-containing aromatic heterocyclic rings to the coupling position can also be attained according to the following schematic:

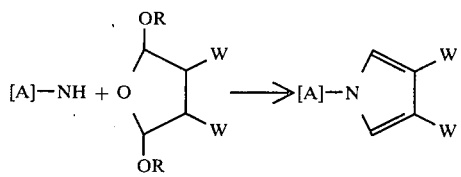

wherein the —NH$_2$ group is substituted in the coupling position, R represents a lower alkyl group having 1 to 4 carbon atoms such as a methyl group, an ethyl group, etc., and [A] and W are the same as defined before. This reaction between an amino group containing compound and a 2,4-dialkoxytetrahydrofuran is described in *Organic Synthesis*, 47, p. 81 (1967).

The coupler of the present invention can advantageously be mixed with a solvent dispersion by dissolving the coupler in a water-immiscible organic solvent having a melting point of about 170° C. or higher, a low-boiling organic solvent or a water-soluble organic solvent, or in a high-boiling, water-immiscible organic solvent and/or a low-boiling and/or water-soluble organic solvent.

Any of the high-boiling, water-immiscible organic solvents described in U.S. Pat. No. 2,322,027 can be used as a solvent. Preferred solvents include di-n-butyl phthalate, benzyl phthalate, triphenyl phosphate, tri-o-cresyl phosphate, diphenyl mono-p-t-butylphenyl phosphate, monophenyl di-o-chlorophenyl phosphate, dioctyl phthalate, dibutyl sebacate, acetyl tributyl citrate, tri-t-octyl trimellitate, n-nonylphenol, dioctylbutyl phosphate, N,N-diethyllaurylamide, 3-pentadecylphenyl ethyl ether, 2,5-di-sec-amyl-phenyl butyl ether, etc.

Low-boiling organic solvents (having a boiling point of not higher than about 170° C.) or water-soluble organic solvents usable together with or in place of the high-boiling solvents are described in U.S. Pat. Nos. 2,801,171, 2,801,170, 2,949,360, etc. Examples of these organic solvents include the following solvents.

(1) Low-boiling, substantially water-insoluble organic solvents such as methyl acetate, ethyl acetate propyl acetate, butyl acetate, isopropyl acetate, ethyl propionate, sec-butyl alcohol, ethyl formate, butyl formate, nitromethane, nitroethane, carbon tetrachloride, chloroform, etc., (2) Water-soluble organic solvents such as methyl isobutyl ketone, β-ethoxyethyl acetate, β-ethoxyethyl acetate, tetrahydrofurfuryl adipat Carbitol acetate (ethyleneglycol monoacetate), methoxytriglycol acetate, methyl Cellosolve acetate, acetylacetone, diacetonealcohol, butyl Carbitol, butyl Cellosolve, methyl Carbitol, methyl ethyl ketone, methanol, ethanol, acetonitrile, dimethylformamide, dioxane, etc.

The water content present in the solvent solution should be sufficiently low enough that the solubility of the coupler is not affected.

After production, the low-boiling or water-soluble solvent can be removed from a cooled noodle-like dispersion by air-drying or continuously washing with water as described in, e.g., U.S. Pat. No. 2,801,171.

A homogenizer for emulsification, a colloid mill, an ultrasonic wave emulsifying apparatus, etc. are useful for dispersing oil-soluble couplers. Diffusion-resistant couplers having a caboxylic acid group or a sulfonic acid group in their molecule together with a ballasting group are soluble in a neutral or a weakly alkaline aqueous solution. These couplers can be incorporated into a photographic emulsion by adding an aqueous solution thereof to the photographic emulsion. These couplers are believed to be rendered diffusion-resistant through formation of micelles in a hydrophilic high molecular weight material.

Examples of couplers of the present invention include the following compounds but the present invention is not to be construed as being limited to these couplers.

Coupler (1)
  1-(2,4,6-Trichlorophenyl)-3-[α-(2,4-di-tert-amylphenoxy)butyramido]-4-(1-imidazolyl)-5-oxo-2-pyrazoline Coupler (2)
  1-(2,4,6-Trichlorophenyl)-3-(2-chloro-5-tetradecanamidoanilino)-4-(1-imidazolyl)-5-oxo-2-pyrazoline Coupler (3)
  1-(2,4,6-Trichlorophenyl)-3-{3-[α-(2,4-di-tert-amylphenoxy)butyramido]benzamido}-4-(2-methyl-1-imidazolyl)-5-oxo-2-pyrazoline Coupler (4)
  1-(2,4,6-Trichlorophenyl)-3-{3-[α-(2,4-di-tert-amylphenoxy)butyramido]phenylureido}-4-(2-methylthio-1-imidazolyl)-5-oxo-2-pyrazoline Coupler (5)
  1-(2,6-Dichloro-4-methoxyphenyl)-3-{3-[α-(3-tert-butyl-4-hydroxyphenoxy)tetradecanamido]benzamido}-4-(2-phenyl-1-imidazolyl)-5-oxo-2-pyrazoline Coupler (6)
  1-(2,4,6-Trichlorophenyl)-3-{3-[α-(2,4-di-tert-amylphenoxy)butyramido]anilino}-4-(1-pyrrolyl)-5-oxo-2-pyrazoline Coupler (7)
  1-{4-[α-(2,4-Di-tert-amylphenoxy)butyramido]phenyl}-3-methyl-4-(1-imidazolyl)-5-oxo-2-pyrazoline Coupler (8)
  1-(2,4,6-Trichlorophenyl)-3-{3-[α-(3-pentadecylphenoxy)butyramido]benzamido}-4-(1-imidazolyl)-5-oxo-2-pyrazoline Coupler (9)
  1-(2,4,6-Trichlorophenyl)-3-[N-trichloroacetyl-(2-chloro-5-tetradecanamido)anilino]-4-(1-imidazolyl)-5-oxo-2-pyrazoline Coupler (10)
  1-(2,4,6-Trichlorophenyl)-3-(3,5-dicarboxyanilino)-4-(4-tetradecanamido-1-imidazolyl)-5-oxo-2-pyrazoline Coupler (11)
  1-(2,4,6-Trichlorophenyl)-3-{3-[α-(3-pentadecylphenoxy)butyramido]benzamido}-4-(3,4-dichloro-1-pyrrolyl)-5-oxo-2-pyrazoline Coupler (12)
  1-{4-[α-(2,4-Di-tert-amylphenoxy)butyramido]phenyl}-3-(2,4-dichloroanilino)-4-(1,2,4-triazol-4-yl)-5-oxo-2-pyrazoline Coupler (13)
  1-Benzyl-3-[α-(2,4-Di-tert-amylphenoxy)butyramido]-4-(1-imidazolyl)-5-oxo-2-pyrazoline Coupler (14)
  1-(2,6-Dichloro-4-methoxyphenyl)-3-[3-(2-carboxymethyl-2-nonadecenamido)benzamido]-4-(1-imidazolyl)-5-oxo-2-pyrazoline Coupler (15)
  2-(4-Methoxy-3-tetradecanamido)anilino-3-(1-imidazolyl)-3H-pyrazolo(1,5a)benzimidazole Coupler (16)
  1-(2,4,6-Trichlorophenyl)-3-{2-chloro-5-[α-(2,4-di-tert-amylphenoxy)butyramido]anilino}-4-(1-imidazolyl)-5-oxo-2)pyrazoline Coupler (17)
  1-(2,4,6-Trichlorophenyl)-3-(2-chloro-5-tetradecycloxycarbamidoanilino)-4-(1-imidazolyl)-5-oxo-2-pyrazoline Typical examples of the synthesis of the photographic couplers of the present invention are described below. Unless otherwise indicated herein, all parts, percents, ratios and the like are by weight.

SYNTHESIS EXAMPLE 1

Production of 1-(2,4,6-Trichlorophenyl)-3-[α-(2,4-di-tert-amylphenoxy)butyramido]-4-(1-imidazolyl)-5-oxo-2-pyrazoline [Coupler (1)]

66 g (0.1 mol) of 1-(2,4,6-trichlorophenyl)-3-[α-(2,4-di-tert-amylphenoxy)butyramido]-4-bromo-5-oxo-2-pyrazoline and 27.2 g (0.4 mol) of imidazole were well mixed with each other in a mortar, then stirred for 2 hours under heating to 100° C. To the reaction mixture was added 200 ml of methanol to prepare a solution. Then 1 liter of ethyl acetate was added thereto, followed by washing several times with water. The ethyl acetate layer was dried with anhydrous sodium sulfate, and concentrated. Upon crystallization of the residue from acetonitrile-ethyl acetate (volume ratio:20.1), 48 g of pure Coupler (1) was obtained. The melting point of the coupler was 185°–187° C.

Elemental Analysis

Calcd. for $C_{32}H_{38}N_5O_3Cl_3$(%): H, 5.87:C, 57.9:N, 10.8; Found (%): H, 5.73:C, 57.86:N, 10.5

SYNTHESIS EXAMPLE 2

Production of 1-(2,4,6-Trichlorophenyl)-3-(2-chloro-5-tetradecanamidoanilino)-4-(1-imidazolyl)-5-oxo-2-pyrazoline [Coupler (2)]:

Step 1: Synthesis of 1-(2,4,6-Trichlorophenyl)-3-[N-ethoxycarbonyl(2-chloro-5-tetradecanamido)anilino]-5-oxo-2-pyrazoline [Intermediate 1]:

124 g (0.2 mol) of 1-(2,4,6-trichlorophenyl)-3-(2-chloro-5-tetradecanamido)anilino-5-oxo-2-pyrazoline was dissolved in 500 ml of toluene and, after adding thereto 100 g (an about 5-fold amount) of ethyl chlorocarbonate, the mixture was refluxed for 10 hours under heating over an oil bath. After the completion of the reaction, toluene was removed under reduced pressure, and the residue was crystallized from acetonitrile-ethyl acetate (volume ratio: 20:1) to obtain 115 g of Intermediate 1 having a melting point of 135°–136° C.

Step 2: Synthesis of 1-(2,4,6-Trichlorophenyl)-3-[N-ethoxycarbonyl(2-chloro-5-tetradecanamido)anilino]-4-bromo-5-oxo-2-pyrazoline (Intermediate 2):

6.8 g of Intermediate 1 obtained in Step 1 above was dissolved in 100 ml of acetic acid, 820 mg of sodium acetate was added thereto, and 1.6 g of bromine was added dropwise thereto at temperatures between 10° C. and 20° C., followed by stirring well. Upon continuing the stirring for about 1 hour, white crystals precipitated. After completion of the precipitation of the crystals, the crystals were filtered out, washed with 10 ml of acetic acid, and dried well to obtain 6.8 g of Intermediate 2 having a melting point of 75°–76° C.

Step 3: Synthesis of Coupler 2:

7.6 g of Intermediate 2 obtained in Step 2 above was well mixed with 2.9 g of imidazole, and heated to 90° C.–100° C. to melt the mixture. After heating the molten mixture for an additional hour under stirring, 30 ml of methanol was added thereto to form a methanol solution. Then 200 ml of ethyl acetate was added thereto, and the mixture was washed several times with water. After drying the ethyl acetate layer with anhydrous sodium sulfate, the solvent was removed under reduced pressure. The residue was crystallized from acetonitrile-ethyl acetate (volume ratio: 20:1), then recrystallized twice from the same mixed solvent to obtain 3.6 g of Coupler 2 having a melting point of 172°–174° C.

Elemental Analysis

Calcd. for $C_{32}H_{38}N_6O_2Cl_4$(%): H, 5.59; C, 47.1; N, 12.3; Found (%): H, 5,62; C, 47.43; N, 12,25

SYNTHESIS EXAMPLE 3

Production of 1-Benzyl-3-[α-(2,4-di-tert-amylphenoxy)butyramido]-4-(1-imidazolyl)-5-oxo-2-pyrazoline [Coupler (13)]:

66 g of 1-benzyl-3-[α-(2,4-di-tert-amylphenoxy)-butyramido]-4-bromo-5-oxo-2-pyrazoline was reacted with 27 g of imidazole in the same manner as in Synthesis Example 1, processed in the same manner, and crystallized from ethyl acetate to obtain 35 g of Coupler (13) having a melting point of 204°–206° C.

Elemental Analysis

Calcd. for $C_{31}H_{39}N_5O_3$(%): H, 7.36; C, 70.3; N, 13.2; Found (%): H, 7.47; C, 70.39; N, 13.11

The couplers of the present invention are 2-equivalent couplers. That is, they require stoichiometrically only 2 equivalents of silver halide as an oxidizing agent to produce one molecule of dye.

In comparison with conventionally widely used 4-equivalent pyrazolone type couplers, the 2-equivalent couplers of the present invention require only about one-half the amount of silver halide, thus the amount of silver halide incorporated in a light-sensitive material can be reduced to about one-half that amount required with 4-equivalent couplers. Therefore, not only is the production cost of light-sensitive materials reduced, but also light scattering is reduced as well improving the sharpness of the images.

The magenta coupler of the present invention can be converted to an azomethine dye in a high yield through a oxidative coupling reaction wherein exposed silver halide acts as an oxidizing agent. With some conventionally used 4-equivalent couplers, a leuco dye which is an intermediate in dye formation undergoes side reactions with an azine ring or the like being formed, resulting in a low conversion yield to the dye. On the other hand, the magenta couplers of the present invention can be converted to an azomethine dye in high yield since such a reactive intermediate is not formed. As a result, the amount of the magenta-forming coupler used in the color light-sensitive material of the present invention can be reduced, which leads to a reduction in silver halide content and in the thickness of an emulsion layer and thus to a reduction of the production cost of the light-sensitive materials, an improvement in the sharpness and facilitating rapid development processing.

The magenta coupler of the present invention has such a strong coupling activity for an oxidized aromatic primary amine color-developing agent that the oxidation product of a developing agent produced upon color development is rapidly removed, thus accelerating the development of the silver halide emulsion.

With the magenta coupler of the present invention, the process of forming a dye is completed in a color developing bath, which enables the materials to be processed with a bleach-fixing bath containing a weak oxidizing agent such as Fe (III) chelate of ethylene diamine tetraacetic acid (EDTA) or the like and a silver complex salt-forming agent or a ferric salt (e.g., ferric chloride) without using a bleaching bath containing a strong oxidizing agent such as potassium ferricyanide or potassium dichromate. This results in a shortening of the time required for the processing steps of color development and minimizes the problem of environmental pollution due to discharge of processing waste water.

The coupling position substituted magenta couplers of the present invention are less inactivated by the action of carbonyl compounds such as aldehydes or ketones. Conventionally used coupling position unsubstituted magenta couplers are often changed into a compound having a low color reaction activity such as methylol or methylenebis compound when contacted with formaldehyde or the like in the air especially in an emulsion layer, thus failing to attain sufficient coloration through color development. The color light-sensitive material of the present invention has the advantage that it is affected to a much less extent by such chemicals.

The coupling position substituted magenta coupler of the present invention has the property that, when it is used for ordinary color light-sensitive materials as described in the Examples, the coupler has a high stability with the lapse of time and undergoes only a slight reduction in coloring property when stored at a low temperature under high humidity as compared with particularly the above described known couplers. The stability of a color light-sensitive material after production with the lapse of time is one of the most important factors in evaluating the characteristics of light-sensitive materials. Also, colored images resulting from the magenta coupler of the present invention have markedly superior heat-fastness as compared with particularly couplers which are not substituted in the coupling position. Even in comparison with the above-described known couplers with the same pyrazolone nucleus and having a substituent in the 4-position, the colored image from the magenta coupler of the present invention is found to exhibit greater heat resistance.

The couplers in accordance with the present invention can be employed in light-sensitive materials containing a reduced amount of silver halide, i.e., about ½ to about 1/100 as much as the amount of ordinary color light-sensitive materials. With color light-sensitive materials containing a reduced amount of silver halide, sufficient color images can be obtained by, for example, halogenation-bleaching silver deposits formed according to color development and again conducting color development to increase the amount of dye produced (for example, U.S. Pat. Nos. 2,623,822, 2,814,565, etc.), or by employing a development processing utilizing color intensification using peroxides or cobalt complex salts to increase the amount of dye produced (for example, West German Patent Application OLS No. 2,357,694, U.S. Pat. Nos. 3,674,490, 3,761,265, West German Patent Application OLS No. 2,044,833, 2,056,359, 2,056,360, 2,226,770, Japanese Patent OPI No. 9,728/73, and 9,729/73, etc.).

The two-equivalent magenta coupler of this invention can be used together with other magenta couplers, as described in, for instance, U.S. Patent Nos. 2,439,089; 2,369,489; 2,600,788; 3,558,319; 2,311,081; 3,419,391; 3,214,437; 3,006,759; 2,725,292; 3,408,194; 2,908,573; 3,519,429; 3,615,506; 3,432,521; 3,152,896; 3,062,653; 3,582,322; 2,801,171; 3,311,476; British Pat. No. 956,261; Japanese Patent Publication Nos. 2016/1969 and 19032/1971; Japanese Patent Application Nos. 114445/1972; 56050/1973, 45971/1973; 21454/1973; 108798/1973; and 114446/1972 in which the amount of these other magenta couplers employed with the two equivalent magenta couplers of the invention, in general, ranges from about 5 to 80 mole % based on the total amount of the magenta couplers employed; with the magenta-colored couplers, as described in U.S. Pat. Nos. 2,983,608; 2,455,170; 2,725,292; 3,005,712; 3,519,429; and 2,688,539; British Pat. Nos. 800,262 and 2,044,778; and Belgian Pat. No. 676,691, incorporated in an amount from about 2 to 20 mole % to the total amount of the magenta couplers employed; with the so-called development inhibitor releasing type couplers capable of imagewise releasing development inhibiting compounds at development, such as, for instance, the monothio type couplers as described in U.S. Pat. Nos. 3,227,550 and 3,227,554 and British Pat. No. 953,454, the o-aminophenylazo type couplers as described in U.S. Pat. No. 3,148,062, and the couplers as described in Japanese Patent Publication No. 8750/1972 and German Patent Application (OLS) No. 2,163,811, with these DIR couplers generally being incorporated in an amount from about 2 to 20 mole % to the total amount of the magenta couplers employed, and also with the hydroquinone releasing development inhibiting compounds as described in U.S. Pat. No. 3,297,445 and British Pat. No. 1,058,606 in which these hydroquinone compounds can be employed therewith in an amount from about 2 to 20 mole % to the total amount of the magenta couplers employed.

One or more of the above-described couplers and the like can be employed in the same layer to achieve the properties required for light-sensitive materials and, of course, the same compound can be incorporated in two or more different layers. In general, the couplers are coated at a coverage of about $1 \times 10^{-4}$ to $5 \times 10^{-3}$ mol/m$^2$, preferably $3 \times 10^{-4}$ to $2 \times 10^{-3}$ mol/m$^2$.

The light-sensitive material of the present invention advantageously contains a p-substituted phenol derivative in an emulsion layer or an adjacent for the purpose of improving the light fastness of the magenta dye formed or of preventing yellowing or print-out of a coupler remaining in the unexposed areas, color fogging, or the like. Particularly effective p-substituted phenol derivatives are the hydroquinone derivatives described in U.S. Pat. Nos. 2,360,290, 2,418,613, 2,675,314, 2,701,197, 2,704,713, 2,710,801, 2,728,659, 2,732,300, 2,735,765, 2,816,038; the gallic acid derivatives as described in U.S. Pat. Nos. 3,457,079; 3,069,262 and Japanese Patent Publication No. 13,496/68; the p-alkoxyphenol derivatives as described in U.S. Pat. No. 2,735,765 and Japanese Patent Application (OPI) No. 4,738/72; and p-hydroxyphenyl derivatives as described in U.S. Pat. Nos. 3,342,300, 3,573,050, 3,574,627 and Japanese Patent Publication No. 20,977/74.

The silver halide emulsion used in this invention can be prepared by mixing an aqueous solution of a water-soluble silver salt such as silver nitrate and an aqueous solution of a water-soluble halide such as potassium bromide in the presence of a water-soluble polymer such as gelatin. Examples of suitable silver halides are silver chloride, silver bromide, silver chlorobromide, silver iodobromide, silver chloroiodobromide, etc. These silver halide grains can be prepared according to any conventional manner and a so-called single jet system, double jet system, or control double jet system can of course be employed.

Also, two or more silver halide emulsions prepared separately can be mixed to produce a silver halide emulsion. Furthermore, the silver halide grains used in this invention can have a uniform crystal structure throughout the entire grain or have a layer structure wherein the interior has a different structure than that of the outer portion of the grain. Furthermore, the silver halide grains can be the so-called conversion type silver halide grains as described in British Pat. No. 635,841 and U.S. Pat. No. 3,622,318. Moreover, the silver halide grains can be the type wherein a latent image is mainly formed on the surfaces of the grains or the type wherein a latent image is mainly formed in the interior of the grains. These silver halide photographic emulsions can be prepared by various methods, such as an ammonia method, a neutralization method, an acid method, etc.

The silver halide emulsion used in this invention can be chemically sensitized. Example of the chemical sensitizers which can be used for the purpose are, for instance, gold compounds such as auric acid chloride, gold trichloride, etc., as described in U.S. Pat. Nos. 2,399,083; 2,540,085; 2,597,856; and 2,597,915, salts of noble metals such as platinum, palladium, iridium, rhodium, ruthenium, etc., as described in U.S. Pat. Nos. 2,448,060; 2,540,086; 2,566,245; 2,566,263; 2,598,079, etc., sulfur compounds capable of forming silver sulfite by reaction with silver salts as described in U.S. Pat. Nos. 1,544,944; 2,410,689; 3,189,458; and 3,501,313, and stannous salts, amines and other reductive materials as described in U.S. Pat. Nos. 2,488,850; 2,518,698; 2,421,925; 2,521,026; 2,694,637; 2,983,610 and 3,201,254.

The hydrophilic colloids which can be used as the vehicle for the silver halide in this invention include gelatin, colloidal albumin, casein, carboxymethyl cellulose, hydroxyethyl cellulose, agar, sodium alginate, starch derivatives, synthetic hydrophilic collids, e.g., polyvinyl alcohol, poly-N-vinyl pyrrolidone, polyacrylic acid copolymers, polyacrylamide and the derivatives and the partially hydrolized products thereof. If desired, a mixture of two or more these colloids which are compatible with each other can be used. Of the above-described colloids, gelatin is most generally used but a part or all of the gelatin can be replaced with a synthetic polymer. Furthermore, a so-called gelatin derivative, that is to say, gelatin modified by treating the gelatin with a compound having a group capable of reacting with the functional groups of the gelatin molecule, i.e., an amino group, an imino group, a hydroxyl group, and a carboxyl group, or also a graft polymer of gelatin formed by bonding the molecular chain of another polymer to the gelatin can be substituted for a part or all of the gelatin.

The silver halide photographic emulsion used in this invention can be subjected to a spectral sensitization or dye sensitization using cyanine dyes such as cyanine, merocyanine, carbocyanine dyes individually or as a combination thereof. These dye sensitization techniques are well known as disclosed in U.S. Pat. Nos. 2,688,545; 2,912,329; 3,397,060; 3,615,635; 3,628,964; British Pat. Nos. 1,195,302; 1,242,588; and 1,293,862, German Patent Application (OLS) Nos. 2,030,326 and 2,121,780, and Japanese Patent Publication Nos. 4936/1968 and 14030/1969. They can be selected appropriately according to the wave length region to be sensitized, the sensitivity deisred and the purposes and uses of the color photographic materials.

Furthermore, various additives can be further added to the above-described photographic emulsions for preventing a reduction in sensitivity of the color photographic materials and a formation of fog during the production, storage, and processing of the color photographic materials.

These additives include 4-hydroxy-6-methyl-1,3,3a,7-tetraazaindene, 3-methylbenzothiazole, 1-phenyl-5-mercaptotetrazole as well as many other heterocyclic compounds, mercury-containing compounds, mercapto compounds, and metal salts.

The silver halide emulsion further can be hardened using conventional methods. Hardening agents which can be used include aldehyde compounds such as formaldehyde, glutaraldehyde, etc.; ketone compounds such as diacetyl and cyclopentadione; bis(2-chloroethylurea); 2-hydroxy-4,6-dichloro-1,3,5-triazine; compounds having reactive halogens as described in U.S. Pat. Nos. 3,288,775 and 2,732,303 and British Pat. Nos. 974,723 and 1,167,207; divinyl sulfone, 3-acetyl-1,3-diacryloylhexahydro-1,3,5-triazine; and also the various compounds described in U.S. Pat. Nos. 3,635,718 and 3,232,763; British Pat. No. 994,869; and U.S. Pat. Nos. 2,732,316; 2,586,168; 3,103,437; 3,017,280; 2,983,611; 2,725,294; 2,725,295; 3,100,704; 3,091,537; 3,321,313; and 3,543,292.

The above-described silver halide emulsions can further contain surface active agents, either individually or as a mixture thereof. These surface active agents can be used as coating aids, dispersing agents, and sensitizers as well as for improving the photographic characteristics, static prevention, and adhesion prevention. These surface active agents include natural surface active agents such as saponin, etc.; nonionic surface active agents such as alkylene oxides, glycerins, glycidols, etc.; anionic surface active agents such as higher alkylamines, quaternary ammonium salts, pyridine, other heterocyclic compounds, phosphoniums and sulfoniums; and amphoteric surface active agents such as aminoacids, aminosulfonates, sulfuric acid esters or phosphoric acid esters of aminoalcohols, etc.

Some specific examples of surface active agents which can be used in this invention are illustrated in U.S. Pat. Nos. 2,271,623; 2,240,472; 2,288,226; 2,739,891; 3,068,101; 3,158,484; 3,201,253; 3,210,191; 3,294,540; 3,415,649; 3,441,413; 3,442,654; 3,475,174; and 3,545,974, German Patent Application (OLS) No. 1,942,665, and British Pat. Nos. 1,077,317 and 1,198,450.

The photographic light-sensitive material of the present invention comprises a support having thereon a silver halide emulsion layer containing a 2-equivalent magenta coupler in accordance with the present invention. One embodiment of the photographic light-sensitive material of the present invention, comprises a multi-layered, multi-colored photographic light-sensitive material comprising a support having thereon a blue-sensitive silver halide emulsion layer containing a yellow color-forming coupler, a green-sensitive silver halide emulsion layer containing a magenta color-forming coupler in accordance with the present invention, and a red-sensitive silver halide emulsion layer containing a cyan color-forming coupler. Known blue-sensitive silver halide emulsions and the red-sensitive silver halide emulsions can be appropriately used. Open-chain type ketomethylene compounds represented by benzoylacetanilides and pivaloylacetanilides can advantageously be used as yellow color-forming couplers. Phenolic or naphtholic compounds can advantageously be used as cyan color-forming couplers. These color-forming couplers can contain a coupling off group on the carbon atom of the coupling position. These color-forming couplers are desirably non-diffusible.

Open-chain type diketomethylene compounds are generally used as yellow couplers. These compounds are described in, for instance, U.S. Pat. Nos. 3,341,351; 3,253,924; 3,384,657; 2,778,658; 2,908,575; 3,227,550; 2,875,057; 3,551,155, German Patent Application (OLS) No. 1,547,868, U.S. Pat. Nos. 3,265,506; 3,582,322; and 3,725,072, German Patent Application (OLS) No. 2,162,899, U.S. Pat. Nos. 3,369,895; 3,227,155; 3,447,928; 3,415,652; and 3,408,194, and German Patent Application (OLS) Nos. 2,057,941; 2,213,461; 2,219,917; 2,261,361; and 2,263,875. Typical examples of suitable yellow couplers which can be used include the following couplers

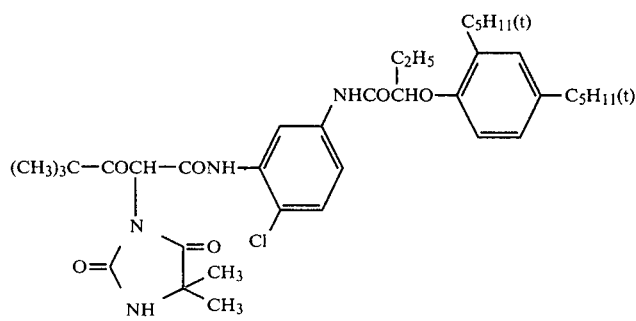

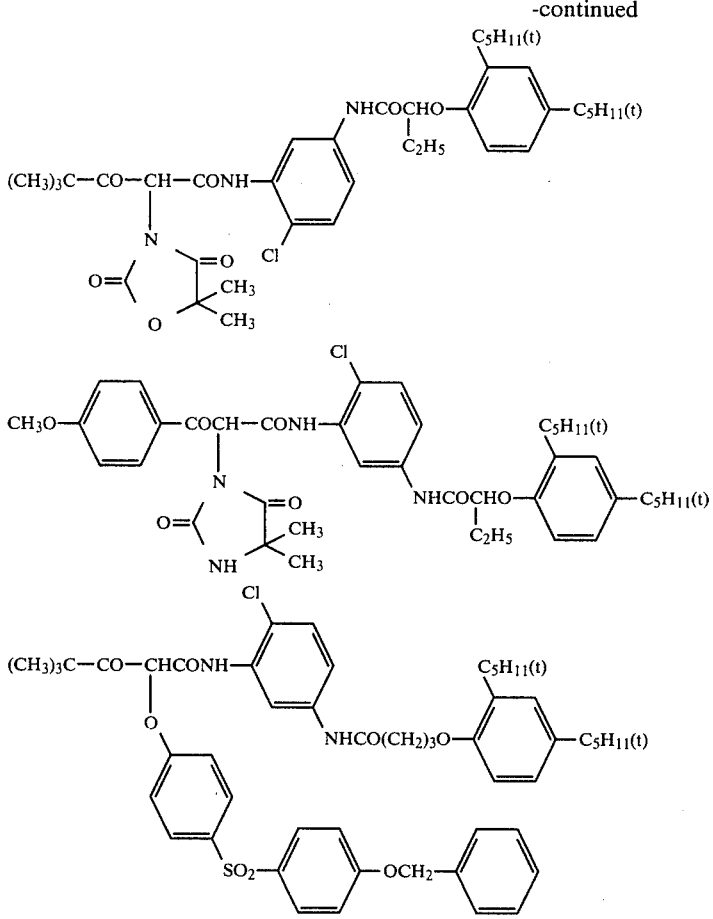

Also, phenol derivatives or naphthol derivatives are mainly used as cyan couplers for color photographic materials. Examples of such derivatives are described in, for instance, U.S. Pat. Nos. 2,369,929; 2,474,293; 2,908,573; 3,619,196; 3,253,294; 3,227,550; 3,419,390; 3,476,563; 2,698,794; 2,895,826; 3,311,476; 3,458,315; 2,423,730; 2,801,171; 3,046,129; 3,516,831; 2,772,162; 3,560,212; 3,582,322; 3,591,383; 3,386,301; 3,632,347; 3,652,286; 3,779,763; 2,434,272; 2,706,684; 3,034,892; 3,583,971; German Patent Application (OLS) Nos. 2,163,811 and 2,207,468, Japanese Patent Publication Nos. 28836/1970 and 27563/1964, and Japanese Patent Application No. 33238/1973. Typical examples of suitable cyan couplers which can be used include the following couplers

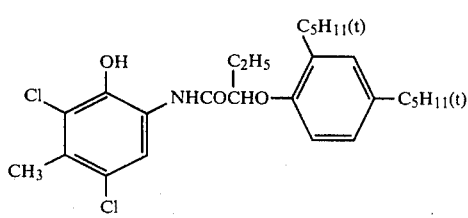

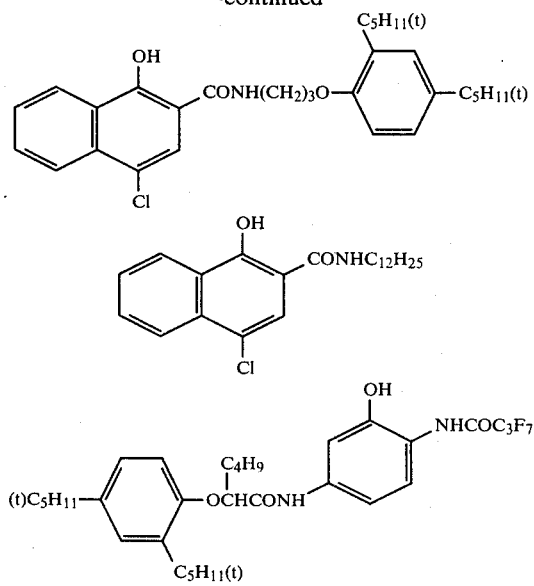

The color photographic material of this invention can contain in the protective layer, interlayers, silver halide emulsion layers, and back layer thereof the ultraviolet absorbents as described in, for instance, U.S. Pat. Nos. 2,685,512; 2,739,888; 2,784,087; 3,253,921; 3,533,794; 3,738,837; and 3,754,919.

The photographic silver halide emulsions are coated on a substantially planar material which does not undergo any substantial dimensional change during processing such as a rigid support, e.g., glass, metal and ceramics, or a flexible support. Typical examples of flexible supports are cellulose acetate films, cellulose nitrate films, cellulose acetate butyrate films, cellulose acetate propionate films, polystyrene films, polyethylene terephthalate films, polycarbonate films, laminates of these films, thin glass sheets, and papers. Furthermore, barytacoated papers and papers coated or laminated with an olefinic polymer such as, in particular, polyethylene, polypropylene, an ethylene-butene copolymer, and a polymer of an α-olefin having 2 to 10 carbon atoms can be also used as the flexible support. Also, a synthetic resin film having a roughened surface for improving the adhesive property to other polymers and improving also the printability as described in Japanese Patent Publication No. 19068/1972 can be used. These supports can be transparent or opaque according to the purpose of the photographic materials and also the transparent support can be colorless or can be colored with a dye or pigment.

Suitable opaque supports include papers which are intrinsicly opaque, transparent films opacified with a dye or a pigment such as titanium oxide, the surface treated synthetic resin films as shown in Japanese Patent Publication No. 19068/1972, and papers and synthetic resin films which were rendered completely light-shielding by adding carbon black or dyes. When the adhesion between the support and the silver halide photographic emulsion layer is insufficient, a layer having high adhesion to the both the support and the emulsion layer can be formed on the support as a subbing layer. Also, for improving the adhesion of the support, the surface of the support can be pre-treated with, for instance, a corona discharge, ultraviolet radiation, a flame treatment, etc. A suitable silver halide coating amount in one emulsion layer can range from about $5 \times 10^{-5}$ to $10^{-6}$ mole/m$^2$.

The photographic light-sensitive material of the present invention can be suitably used for various use such as color positive films, color negative films, color reversal films, color photographic printing papers, etc.

The color photographic light-sensitive material of the present invention provides magenta color images having excellent spectral properties and image fastness when imagewise exposed in a conventional manner and processed using conventional color processing steps.

The development process includes fundamentally a color development step, a bleach step, and a fixing step with washing therebetween, if necessary. In this case, each step can be applied independently or two or more of these steps can be performed together using a processing solution with these functions. For instance, the bleach step and the fix step can be carried out in one step using a blix bath. Furthermore, each step can be, if desired, carried out as two or more steps or further the development process can be carried out using the combination of a color development step, a first fixing step, and blixing step. Furthermore, the development process can include further, if desired, a prehardening bath, a neutralization bath, a first development (black & white development) a image stabilization bath, and a washing. The processing temperature is determined appropriately according to the kind of photographic materials and the processing steps and sometimes the temperature is lower than about 18° C. but usually is higher than about 18° C. Ordinary processing temperatures are about 20° to 60° C. and recently about 20° to 60° C. and recently about 30° to 60° C. In addition, it is not always necessary to carry out all of the processing steps at the same temperature.

The color developer used for the development is an alkaline aqueous solution containing a developing agent of which the oxidation product forms a dye-forming compound by reaction with a coupler and having a pH of higher than about 8, preferably a pH of 9 to 12.

The above-described color developing agent is a compound having a primary amino group and the ability to develop exposed silver halide or a precursor thereof capable of forming such a compound. Typical examples of suitable developing agents are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-diethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfoamidoethyl-N,N-diethylaniline, and the salts (e.g., sulfates, hydrochlorides, sulfites, p-toluenesulfonates, etc.) thereof. Other examples of developing agents are described in U.S. Pat. Nos. 2,193,015 and 2,592,364, Japanese Patent Application (OPI) No. 64933/1973, and L. F. A. Mason, *Photographic Processing Chemistry*, pages 226–229, Focal Press, London (1966). Also, the above described compounds can be used together with 3-pyrazolidones.

The color developer can, if desired, contain various additives. Main examples of these additives are alkalis (e.g., the hydroxides, carbonates, and phosphates of alkali metals and ammonia), pH controlling agents or buffers (e.g., weak acids such as acetic acid and boric acid, weak bases, and the salts thereof), development accelerators (e.g., the pyridinium compounds and cationic compounds as described in U.S. Pat. Nos. 2,648,604 and 3,671,247; potassium nitrate and sodium nitrate; the polyethylene glycol condensates and the derivatives thereof as described in U.S. Pat. Nos. 2,533,990; 2,577,127 and 2,950,970; nonionic compounds such as polyethio ethers as described in British Pat. No. 1,020,032; polymers containing a sulfite ester group as described in U.S. Pat. No. 3,068,097; organic amines such as pyridine and ethanolamine; benzyl alcohol; and hydrazines), antifoggants (e.g., alkali metal bromides; alkali metal iodides; nitrobenzoimidazoles, 5-methylbenzotriazoles, and 1-phenyl-5-mercaptobenztriazoles as described in U.S. Pat. Nos. 2,496,940 and 2,656,271; compounds for rapid processing as described in U.S. Pat. Nos. 3,113,864; 3,342,596; 3,295,976; 3,615,522; and 3,597,199; thiosulfonyl compounds as described in British Pat. No. 972,211; the phenazine-N-oxides as described in Japanese Patent Publication No. 41675/1971; and the antifoggants as described in *Kagaku Shashin Brinran (Handbook of Photographic Science)*, 2nd Vol. pages 29–47), stain- or sludge-preventing agents as described in U.S. Pat. Nos. 3,161,513 and 3,161,514 and British Pat. Nos. 1,030,442; 1,144,481; and 1,251,558, the multilayer effect promotors as disclosed in U.S. Pat. No. 3,536,497, and preservatives (e.g., sulfites, acid sulfites, hydroxylamine hydrochloride, formsulfite, alkanolamine-sulfite addition products).

The silver halide photographic material is subjected to a bleach treatment in a conventional manner after the color development and the bleach treatment can be carried out separately from or simultaneously with the fix treatment. If described, a fixing agent can be added to the bleach solution to provide a blix solution. Examples of suitable bleaching agents are ferricyanides, dichromates, water-soluble cobalt (III) salts, water-soluble copper (II) salts, water-soluble quinones, nitrosophenols, compounds of polyvalent metals such as iron (III), cobalt (III), and copper (II), the complex salts of these polyvalent metal cations and organic acids (e.g., the metal complex salts of ethylenediamine tetraacetic acid, nitrilotriacetic acid, iminodiacetic acid, N-hydroxyethyl ethylenediaminetriacetic acid, malonic acid, tartaric acid, malic acid, diglycolic acid, and dithioglycolic acid and the copper complex salt of 2,6-dipicolinic acid), peracids (e.g., alkylperacids, persulfates, permanganates, hydrogen peroxide), and hypochlorites, chlorine, bromine, etc. They can be used individually or as a mixture thereof.

Furthermore, the processing solution used for bleaching or blixing can further contain the bleach accelerators as described in U.S. Pat. Nos. 3,042,520 and 3,241,966 and Japanese Patent Publication Nos. 8506/1970 and 8836/1970.

Also, the present invention can be employed in other various photographic materials including color direct positive photographic materials, diffusion transfer color photographic materials, and monochromatic photographic materials.

By applying the method as described in U.S. Pat. Nos. 2,439,901; 2,623,822; 2,814,565; and 3,372,028 in which the developed silver formed by color development is subjected to a halogenation bleach and then color development again to increase the amount of the dye formed or the method as described in Japanese Patent Application (OPI) No. 9728/1973 in which the amount of silver halide in the color photographic material is reduced by a color intensifying method to the color photographic materials containing the couplers of this invention, better results can be obtained.

Somes of the advantages of the present invention are as follows.

(1) Since the amount of silver necessary for obtaining the same magenta color image density can be reduced, the thickness of the light-sensitive layer containing the coupler can be reduced, thus improving the sharpness of the images.
(2) The heat fastness of the magenta color images produced using the coupler of the present invention is improved.
(3) The production cost can be reduced through the reduction in the amount of silver halide necessary.
(4) Magenta couplers stable to chemicals such as formaldehyde or acetone can be obtained.
(5) Couplers having a high developing activity can be obtained.
(6) Color images with less fog and stain and with excellent other photographic properties can be obtained.
(7) Silver halide color photographic light-sensitive materials having excellent storage stability can be obtained using the coupler of the present invention.
(8) The conversion of the coupler to the dye is improved using the coupler of the present invention.

The light-sensitive materials of the present invention having the above-described advantages are extremely useful in the field of color photography.

The present invention will now be illustrated in more detail by the following non-limiting examples of preferred embodiments of the present invention.

EXAMPLE 1

A solution, prepared by heating at 60° C. and dissolving a mixture comprising 23.4 g of Coupler (8) in accordance with the present invention, 24 ml of dioctyl butyl phosphate and 60 ml of ethyl acetate, was added to 250 ml of a 60° C. aqueous solution containing 2.5 g of gelatin and 0.75 g of sodium dodecylbenzenesulfonate. The resulting solution was mechanically vigorously stirred using a homogenizer to obtain a coupler emulsion dispersion. This emulsion dispersion was mixed with 200 g of a photographic emulsion containing $11.2 \times 10^{-2}$ mol of silver chlorobromide (silver bromide: 45 mol%, silver chloride: 55 mol %) and 20 g of gelatin. Then, 10 ml of a 3% acetone solution of triethylenephosphoramide was added thereto as a hardener and, after adjusting the final pH to 6.5, the solution was coated on a cellulose triacetate film support in a dry thickness of 4.5μ. (Film A) This film contained $1.55 \times 10^{-3}$ mol/m$^2$ of Coupler (8) and $6.2 \times 10^{-3}$ mol/m$^2$ of silver chlorobromide.

For the purpose of comparison, 21.6 g of corresponding coupling position unsubstituted coupler, 1-(2,4,6-trichlorophenyl)-3-{3-[α-(3-n-pentadecylphenoxy)-butyramido]-benzamido}-5-oxo-2-pyrazoline (Comparison Coupler A), was dispersed in place of the above-described Coupler (8) in the same manner as described above, mixed with 400 g of an emulsion having the same composition as above, and coated on a film in a dry thickness of 5.2μ (Film B). This film contained $1.57 \times 10^{-3}$ mol/m$^2$ of the coupler and $12.6 \times 10^{-3}$ mol/m$^2$ of silver chlorobromide.

These films were subjected to stepwise exposure and the following development processing.

| Color Development Processing: | | |
|---|---|---|
| 1. Color Development | 21° C. | 12 min. |
| 2. Washing | " | 30 sec. |
| 3. First Fixing | " | 4 min. |
| 4. Washing | " | 4 min. |
| 5. Bleaching | " | 8 min. |
| 6. Washing | 21° C. | 4 min. |
| 7. Second Fixing | " | 4 min. |
| 8. Washing | " | 6 min. |

The processing solutions had the following compositions.

| Color Developer | | |
|---|---|---|
| Sodium Hexametaphosphate | 2 | g |
| Sodium Sulfate (anhydrous) | 2 | g |
| Benzyl Alcohol | 5 | ml |
| Sodium Carbonate (monohydrate) | 27.5 | g |
| Potassium Bromide | 0.5 | g |
| Hydroxylamine Sulfate | 2.5 | g |
| N-Ethyl-N-(β-methanesulfon-amidoethyl)-3-methyl-4-amino-aniline Sesquisulfate | 2.5 | g |
| Water to make | 1 | liter |
| | (pH = 10.7) | |
| Fixing Solution | | |
| Sodium Thiosulfate (hexahydrate) | 80 | g |
| Sodium Sulfite (anhydrous) | 5 | g |
| Borax | 6 | g |
| Glacial Acetic Acid | 4 | ml |
| Potassium Alum | 7 | g |
| Water to make | 1 | liter |

|  |  |  |
|---|---:|---|
| Bleaching Bath (pH = 4.5) |  |  |
| Potassium Ferricyanide | 100 | g |
| Potassium Bromide | 5 | g |
| Boric Acid | 10 | g |
| Borax | 5 | g |
| Water to make | 1 | liter |
|  | (pH = 7.2) |  |

After processing, the optical density of these film samples was measured using green light. As a result, distinct color images having the photographic properties as shown in Table 1 and having an absorption maximum at 542 mμ were obtained.

TABLE 1

| Film | Coupler | Coupler Amount (mol/m²) Coupler | Coupler Amount (mol/m²) AgX | Ag/Coupler (molar ratio) | Film Thickness (μ) | Fog | Gamma | Relative Sensitivity | Maximum Color Density |
|---|---|---|---|---|---|---|---|---|---|
| A | (8) | $1.55 \times 10^{-3}$ | $6.2 \times 10^{-3}$ | 4 | 4.5 | 0.02 | 3.20 | 100 | 3.35 |
| B | A | $1.57 \times 10^{-3}$ | $12.6 \times 10^{-3}$ | 8 | 5.2 | 0.02 | 2.25 | 95 | 2.40 |

The relative sensitivity was exposure amount necessary for providing a density of fog+0.1.

The results in Table 1 show that the coupler of the present invention provided higher sensitivity, higher gradation and higher maximum color density even when the ratio of silver halide/coupler was reduced to about ½.

The above-described results shows that the coupler of the present invention enables the amount of silver deposit necessary for obtaining a dye image of definite density to be reduced i.e., that the amount of coated silver halide and the amount of coupler necessary for obtaining a certain maximum color density can be reduced and the developing time can be shortened.

When Coupler (1) of the present invention was emulsified and coated in a similar manner, a distinct color image having an maximum absorption at 545 mμ was obtained. Also, excellent photographic properties were obtained even when the amount of coated silver was small.

EXAMPLE 2

The following processings were conducted after exposure of Films A and B described in Example 1.

| Color Development Processing |  |  |
|---|---|---|
| 1. Color Developing Processing | 30° C. | 4 min. |
| 2. Bleach-Fixing | " | 2 min. |
| 3. Washing | " | 2 min. |
| 4. Stabilizing Bath | " | 2 min. |

The photographic properties of the thus obtained films are shown in Table 2 below.

Furthermore, as aqueous stabilizing baths a formaldehyde free Stabilizing Bath (a) and Stabilizing Bath (b) containing 1% of a 40% by weight aqueous solution of formaldehyde were used. With the two films having been processed, the reduction ratio of the density, based on the initial density, after leaving the films at 80° C. for 1 week was determined and the results are tabulated in Table 3 below.

|  |  |  |
|---|---:|---|
| Color Developer |  |  |
| Sodium Metaborate | 25 | g |
| Sodium Sulfite | 2 | g |
| Hydroxylamine (sulfate) | 2 | g |
| Potassium Bromide | 0.5 | g |
| 6-Nitrobenzimidazole (sulfate) | 0.02 | g |
| Sodium Hydroxide | 4 | g |
| Benzyl Alcohol | 15.8 | ml |
| Diethylene Glycol | 20 | ml |
| 4-(N-Ethyl-N-β-methanesulfon-amidoethyl)amino-2-methyl-aniline Sesquisulfate | 8 | g |
| Water to make | 1 | liter |
| Bleach-fixing Solution |  |  |
| Ferric Salt of Ethylene-diaminetetraacetic Acid | 45 | g |
| Ammonium Thiocyanate | 10 | g |
| Sodium Sulfite | 10 | g |
| Ammonium Thiosulfate (60% aq. soln.) | 100 | ml |
| Sodium Ethylenediaminetetraacetate | 5 | g |
| Water to make | 1 | liter |
|  | (pH = 6.9) |  |
| Stabilizing Bath (a) |  |  |
| Tartaric Acid | 10 | g |
| Zinc Sulfate | 10 | g |
| Sodium Metaborate | 20 | g |
| Water to make | 1 | liter |
| Stabilizing Bath (b) |  |  |
| Tertaric Acid | 10 | g |
| Zinc Sulfate | 10 | g |
| Sodium Metaborate | 20 | g |
| Formalin (40%) | 10 | ml |
| Water to make | 1 | liter |

TABLE 2

| Photographic Properties (using Stabilizing Bath (a)) | | | |
|---|---|---|---|
| Film | Coupler | Fog | Gamma | Maximum Color Density |
| A | (8) | 0.03 | 3.15 | 3.30 |
| B | A | 0.03 | 2.21 | 2.38 |

TABLE 3

Fastness of Color Images (after storage for 1 week at 80° C.)

| Film | Stabilizing Bath | Reduction Ratio (%) in Color Image Density Initial Density 0.5 | 1.0 | 2.0 |
|---|---|---|---|---|
| A | (a) | 12 | 8 | 7 |
|  | (b) | 10 | 6 | 5 |
| B | (a) | 64 | 44 | 11 |
|  | (b) | 12 | 9 | 7 |

The results in Table 2 show that, even when a strong oxidizing agent not used as in the development processing of Example 1, sufficient photographic properties can be obtained using Film A, and that Film A has better properties than those of Film B. The results in Table 3 show that Film A provides sufficient heat fastness even without conducting a stabilization using formaldehyde.

EXAMPLE 3

On a polyethylene resin-coated baryta paper were coated, as a first layer, a blue-sensitive silver chlorobromide emulsion containing α-pivaloyl-α-(2,4-dioxo-5,5-dimethyl-1,3-oxazolidin-3-yl)-2-chloro-5-[α-(2,4-di-tert-amylphenoxy)butyramido]acetanilide in a thickness of 3.0μ (amount of coupler coated: $1.18 \times 10^{-3}$ mol/m$^2$: amount of silver coated: $3.53 \times 10^{-3}$ mol/m$^2$: silver bromide content: 70 mol %: silver chloride content: 30 mol %) and, as a second layer, 2-t-octylhydroquinone-containing gelatin in a thickness of 1.5μ (amount of hydroquinone compound coated: 0.05 g/m$^2$). Further, a mixture of 10.3 g of Coupler (5) of the present invention, 0.8 g of 5-di-t-octylhydroquinone, 0.8 g of 6,6'-dihydroxy-7,7'-dimethyl-4,4,4',4'-tetramethyl-bis-2,2'-spirochroman, 10 ml of tricresyl phosphate and 30 ml of ethyl acetate were heated over a steam bath to dissolve. Then, the resulting solution was added to an aqueous solution containing 10 g of gelatin and 0.5 g of sodium cetylsulfate, followed by vigorous mechanical stirring to obtain a coupler emulsion dispersion. This emulsion dispersion was mixed with 100 g of a photographic emulsion containing $4.7 \times 10^{-2}$ mol of silver chlorobromide (silver chloride: 50 mol %: silver bromide: 50 mol %) and 9 g of gelatin. Then, 3 ml of a 4% aqueous solution of 2-hydroxy-4,6-dichloro-s-triazine sodium salt was added thereto as a hardening agent and, after adjusting the pH to 6.3, the resulting mixture was coated in a dry thickness of 1.9μ as a third layer (amount of coupler coated: $4.7 \times 10^{-4}$ mol/m$^2$; amount of silver coated: $1.88 \times 10^{-3}$ mol/m$^2$). Then, as a fourth layer, gelatin containing 2,5-di-t-octylhydroquinone and 2-(5-chlorobenzotriazole-2-yl)-4-methyl-6-butylphenol (as an ultraviolet light-absorbing agent) and 2-(benzotriazole-2-yl)-4-t-butylphenol was coated in a thickness of 2.5μ (amount of hydroquinone compound coated: 0.05 g/m$^2$; amount of each of the benzotriazole compounds coated: 0.4 g/m$^2$) and, as a fifth layer, a red-sensitive silver halide emulsion containing 2-[α-(2,4-di-t-amylphenoxy)butyramido]-4,6-dichloro-5-methylphenol was coated in a thickness of 2.5μ (amount of coupler coated: $0.98 \times 10^{-3}$ mol/m$^2$; amount of silver coated: $2.94 \times 10^{-3}$ mol/m$^2$; silver bromide content: 50 mol %; silver chloride content: 50 mol %). Then, as an uppermost layer, gelatin was coated in a thickness of 1.0μ to prepare a color print paper (Film C).

For the purpose of comparison, the above procedures were repeated. An emulsion was prepared in the absolutely same manner as described above for the third layer of Film C except for using 9.0 g of a corresponding 4-position unsubstituted comparative coupler, 1-(2,6-dichloro-4-methoxyphenyl)-3-{3-[α-(3-tert-butyl-4-hydroxyphenoxy)tetradecanamido]benzamido}-5-oxo-2-pyrazolone (Comparison Coupler B), in place of Coupler (5), and the resulting mixture was mixed with 200 g of an emulsion having the same composition, as used for the third layer described above. Then, the mixture was coated in a dry thickness of 3.0 to prepare a color print paper (Film D) (amount of coupler coated: $7.5 \times 10^{-4}$ mol/m$^2$; amount of silver coated: $6.0 \times 10^{-3}$ mol/m$^2$).

These samples were subjected to stepwise exposure and to the same development processing as in Example 2 (using stabilizing bath (a)). When the reflection density was measured using green light, distinct color images having the photographic properties as shown in Table 4 and having a main wave-length of 542 mμ were obtained.

TABLE 4

| | | Photographic Properties | | | | | | |
|---|---|---|---|---|---|---|---|---|
| | | Coated Amount (mol/m$^2$) | | AgX/Coupler (molar | | | Relative | Maximum Color |
| Film | Coupler | Coupler | Silver | Ratio) | Fog | Gamma | Sensitive | Density |
| C | (5) | $4.7 \times 10^{-4}$ | $1.88 \times 10^{-3}$ | 4 | 0.07 | 2.43 | 100 | 2.38 |
| D | B | $7.5 \times 10^{-4}$ | $6.0 \times 10^{-3}$ | 8 | 0.06 | 2.45 | 98 | 2.42 |

The results in Table 4 show that the light-sensitive material using the coupler of the present invention provides the same photographic properties as that of a conventional light sensitive material even when the coated amounts of coupler and silver halide are reduced.

Furthermore, with the thus obtained developed films, the light fastness when irradiated for 12 days under a day light-color fluorescent lamp of an illuminance of about 30,000 lux through an ultraviolet high absorbing filter which substantially completely absorbs ultraviolet light not longer than 400 mμ in wavelength, the heat fastness when left for 1 week at 80° C. in a dark place and the humidity fastness when stored for 2 weeks at 60° C. under 75% RH (relative humidity) are tabulated below in terms of a reduction (%) in density based on the initial density.

TABLE 5

| | | Color Image Fastness (Density Reduction Ratio (%)) | | | | | | | | |
|---|---|---|---|---|---|---|---|---|---|---|
| | | Fluorescent Lamp 12 days Initial Density | | | 88° C., 1 week Initial Density | | | 60° C., 75% RH 2 weeks Initial Density | | |
| Film | Coupler | 0.5 | 1.0 | 2.0 | 0.5 | 1.0 | 2.0 | 0.5 | 1.0 | 2.0 |
| C | (5) | 13 | 9 | 4 | 6 | 4 | 3 | 6 | 3 | 2 |
| D | B | 15 | 10 | 5 | 45 | 26 | 6 | 15 | 8 | 4 |

From the above results, it can be seen that color images fast against heat, humidity and light can be formed by using the coupler of the present invention.

EXAMPLE 4

A photographic emulsion containing Coupler (1) of the present invention was coated on a support and, after exposing, processed with a dilute alkaline developer of a pH of 12.5 containing 2 g/liter of Na$_2$SO$_3$ and 8 g/liter of 4-amino-3-methyl-N-(β-hydroxyethyl)aniline monosulfate. This support was intimately contacted with an image-receiving sheet containing dimethyl-β-hydroxyethyl-β-stearoylamidopropylammonium dihydrogenphosphite (mordanting agent) for 3 minutes at 24° C. Upon delaminating the image-receiving sheet after development, the magenta dye formed was transferred to the image-receiving sheet, with a good positive image being obtained.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having thereon at least one silver halide emulsion layer and at least one of said silver halide emulsion layers containing a photographic two-equivalent magenta coupler having the general formula [II] or [III]

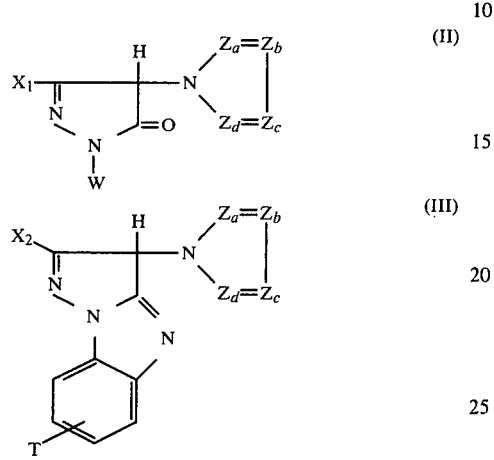

wherein W represents an aryl group having up to 40 carbon atoms, which may be substituted with one or more of an alkyl group, an alkenyl group, a cycloalkyl group, an aralkyl group, a cycloalkenyl group, a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonyl group, an aryloxycarbonyl group, an alkoxy(thiocarbonyl)amino group, an aryloxy(thiocarbonyl)amino group, a sulfamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylamino group, a hydroxy group and a mercapto group;

X₁ has up to 40 carbon atoms and represents an acylamino group;

X₂ has up to 40 carbon atoms and represents an acylamino group, a ureido group, or an anilino group;

T represents a hydrogen atom; or has up to 40 carbon atoms and represents a straight or branched chain alkyl group, an alkenyl group, a cycloalkyl group, an aralkyl group or; a cycloalkenyl group, which may be substituted with one of more of the substituents defined above for the aryl group W; an aryl group which may be substituted with one or more the substituents defined above for the aryl group W, a 5- or 6-membered heterocyclic group containing at least one of an oxygen, sulfur or a nitrogen atom, which may be substituted with one of more of the substituents defined above for the aryl group W; a cyano group, a thiocyano group; an alkoxy group; an aryloxy group; a halogen atom; a carboxy group; an alkoxycarbonyl group; an aryloxycarbonyl group; an acyloxy group; an alkylcarbonyl group; an arylcarbonyl group; an alkylthiocarbonyl group; an arylthiocarbonyl group; a sulfo group; a sulfamoyl group; a carbonyl group; an acylamino group; a diacylamino group; a ureido group; a thioureido group; an alkoxycarbonylamino group; an aryloxycarbonylamino group; an alkoxy (thiocarbonyl)amino group; an aryloxy(thiocarbonyl)amino group; a sulfamido group; an alkylsulfonyloxy group; an arylsulfonyloxy group; an arylsulfonyl group; an alkylsulfonyl group; an arylthio group; an alkylthio group; an alkylsulfinyl group; an arylsulfinyl group; an alkylamino group; a dialkylamino group; an anilino group; an N-arylanilino group; an N-alkylanilino group; an N-acylanilino group; a hydroxy group or a mercapto group; and $Z_a$, $Z_b$, $Z_c$ and $Z_d$ in the

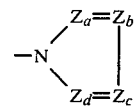

moiety may be the same or different and each represents (a) a methine group, which may be substituted with a substituent having up to 40 carbon atoms and selected from the group consisting of a straight or branched chain alkyl group, an alkenyl group, a cycloalkyl group, an aralkyl group, a cycloalkenyl group, an aryl group, a heterocyclic group, an alkoxycarbonyl group, an aryloxycarbonyl group, an aralkyloxycarbonyl group, an alkoxy group, an aryloxy group, an alkylthio group, a carboxy group, an acylamino group, a diacylamino group, an N-alkylacylamino group an N-arylacylamino group, a ureido group, a thioureido group, an alkoxycarbonylamino group, an aryloxycarbonylamino group, an alkoxy(thiocarbonyl)amino group, an aryloxy(thiocarbonyl)amino group, an anilino group, an alkylamino group, a cycloamino group, an alkylcarbonyl group, an arylcarbonyl group, a sulfonamido group, a carbamoyl group, a sulfamoyl group, a cyano group, an acyloxy group, a sulfonyloxy group, a halogen atom, a sulfo group, and a nitro group; or (b) an —N= group, with the proviso that the nigtrogen-containing heterocyclic moiety formed by $Z_a$, $Z_b$, $Z_c$, $Z_d$ and the nitrogen atom is a monocyclic 5-membered aromatic heterocyclic group.

2. The color photographic light sensitive material of claim 1, wherein said heterocyclic substituent group for the aryl group W and the substituents T is furyl, oxazoyl, benzothiazoyl or imidazoyl.

3. The material as claimed in claim 1, wherein the photographic two-equivalent magenta coupler has the general formula (II)

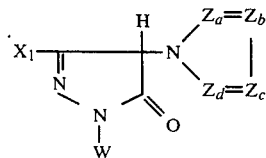

wherein $X_1$, W, $Z_a$, $Z_b$, $Z_c$ and $Z_d$ each has the same meanings as defined in claim 1.

4. The material as claimed in claim 3, wherein W is a phenyl group in which at least one ortho or para position thereof is substituted with an alkyl group, an alkoxy group, an acylamino group or a halogen atom.

5. The material as claimed in claim 3, wherein the

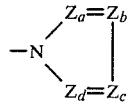

moiety is an imidazolyl group which can be substituted with one or more of the substituents as defined claim 3 for the methine group of $Z_a$ to $Z_d$.

6. The material as claimed in claim 1, wherein the photographic two-equivalent magenta coupler has the general formula (III)

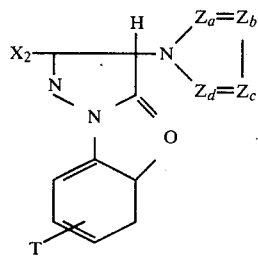

wherein $X_2$ represents an anilino group; the

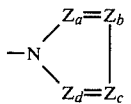

moiety is an imidazolyl group which can be substituted with one or more of the substituents as defined in claim 1 for the methine group of $Z_a$ to $Z_d$; and T is a hydrogen atom or a substituent as defined in claim 1 for T.

7. The material as claimed in claim 3, wherein the

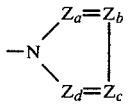

moiety is a 1-imidazolyl group, a 2-methyl-1-imidazolyl group, a 2-methylthio-1-imidazolyl group, a 2-ethylthio-1-imidazolyl group, a 2,4-dimethyl-1-imidazolyl group, a 4-methyl-1-imidazolyl group, a 4-nitro-1-imidazolyl group, a 4-chloro-1-imidazolyl group, a 2-phenyl-1-imidazolyl group, a 4-phenyl-1-imidazolyl group, a 4-acetyl-1-imidazolyl group, a 4-tetradecanamido-1-imidazolyl group, a 1-pyrrolyl group, a 3,4-dichloro-1-pyrrolyl group, a 1-pyrazolyl group, a 1,2,4-triazolyl group, a 1,2,3-1-triazolyl group, or a 1-tetrazolyl group.

8. The material as claimed in claim 3, wherein the monocyclic 5-membered aromatic heterocyclic group is a 1-imidazolyl group, a 2-methyl-1-imidazolyl group, 2-methylthio-1-imidazolyl group, a 2-phenyl-1-imidazolyl group, or 3,4-dichloro-1-pyrrolyl group.

9. The material as claimed in claim 3, the coupler is 1-(2,4,6,-trichlorophenyl)-3-[α-(2,4-di-tert-amylphenoxy)butyramido]-4-(1-imidazolyl)-5-oxo-2-pyrazoline, 1-(2,4,6-trichlorophenyl)-3-{3-[α-(2,4-di-tert-amylphenoxy)-butyramido]-benzamido}-4-(2-methyl-1-imidazolyl)-5-oxo-2-pyrazoline, 1-(2,4,6-trichlorophenyl)-3-{3-[α-(2,4-tert-amylphenoxy)-butyramido]-phenylureido}-4-(2-methylthio-1-imidazolyl)-5-oxo-2-pyrazoline, 1-(2,6-dichloro-4-methoxyphenyl)-3-{3-[α-(3-tert-butyl-4-hydroxyphenoxy)tetradecanamido]benzamido}-4-(2-phenyl-1-imidazolyl)-5-oxo-2-pyrazoline, 1-(2,4,6-trichlorophenyl)-3-{3-[α-(3-pentadecylphenoxy)butyramido]benzamido}-4-(1-imidazolyl)-5-oxo-2-pyrazoline, 1-(2,4,6-trichlorophenyl)-3-{3-[α-(3-pentadecylphenoxy)butyramido]benzamido}-4-(3,4-dichloro-1-pyrrolyl)-5-oxo-2-pyrazoline, or 1-(2,4-dichloro-4-methoxyphenyl)-3-[3-(2-carboxymethyl-2-nonadecenamido)benzamido]-4-(1-imidazolyl)-5-oxo-2-pyrazoline.

10. The material as claimed in claim 6, the coupler is 2-(4-methoxy-3-tetradecanamido)anilino-3-(1-imidazolyl)-3H-pyrazolo(1,5a)benzimidazole.

11. The material as claimed in claim 1, wherein the silver halide emulsion layers contain at least one blue-sensitive silver halide emulsion layer containing a yellow coupler, at least one green-sensitive silver halide emulsion layer containing the two-equivalent magenta coupler as described in claim 1, and at least one red-sensitive silver halide emulsion layer containing a cyan coupler.

12. A photographic light-sensitive material comprising a support having thereon a blue-sensitive silver halide emulsion layer containing a yellow coupler, a green-sensitive silver halide emulsion layer containing the two-equivalent magenta coupler as described in claim 1, and a red-sensitive silver halide emulsion layer containing a cyan coupler.

* * * * *